(12) United States Patent
Tilson et al.

(10) Patent No.: US 10,188,273 B2
(45) Date of Patent: Jan. 29, 2019

(54) BIOLOGICAL NAVIGATION DEVICE

(75) Inventors: Alexander Quillin Tilson, Burlingame, CA (US); Mark Christopher Scheeff, San Francisco, CA (US); Gene Duval, Menlo Park, CA (US)

(73) Assignee: LOMA VISTA MEDICAL, INC., Tempe, AZ (US)

( * ) Notice: Subject to any disclaimer, the term of this patent is extended or adjusted under 35 U.S.C. 154(b) by 1481 days.

(21) Appl. No.: 12/512,809

(22) Filed: Jul. 30, 2009

(65) Prior Publication Data

US 2010/0099949 A1    Apr. 22, 2010

Related U.S. Application Data

(63) Continuation of application No. PCT/US2008/052542, filed on Jan. 30, 2008.
(Continued)

(51) Int. Cl.
*A61B 1/00* (2006.01)
*A61B 1/005* (2006.01)
(Continued)

(52) U.S. Cl.
CPC .......... *A61B 1/0051* (2013.01); *A61B 1/005* (2013.01); *A61B 1/0008* (2013.01);
(Continued)

(58) Field of Classification Search
CPC .......... A61B 1/00156; A61B 1/00154; A61B 1/0051; A61B 1/0053; A61B 1/0055; A61B 1/0056; A61B 1/0057; A61B 1/0058; A61B 1/008; A61B 1/01; A61B 2017/003; A61B 2017/00305; A61B 2017/00309; A61B 2017/00314; A61B 2017/00318; A61B 2017/00323; A61B 2017/00327; A61B 2017/00331; A61B 2017/00336;
(Continued)

(56) References Cited

U.S. PATENT DOCUMENTS 3,533,578 A    10/1970   Lesh
3,924,632 A    12/1975   Cook
(Continued)

FOREIGN PATENT DOCUMENTS

CA    2304776 C    5/2007
DE    2513018 A    10/1975
(Continued)

OTHER PUBLICATIONS

Bell et al.; Use of a low-pressure 3cm diameter everting (toposcopic) catheter as an aid to intubating the difficult colon—a feasibility study using a plastic model; Abstract T84; British Society of Gastroenterology Annual Meeting (Glasgow); 1 pg.; Mar. 23-25, 1999.
(Continued)

*Primary Examiner* — Ryan Henderson
(74) *Attorney, Agent, or Firm* — King & Schickli, PLLC

(57) ABSTRACT

Biological navigation devices and methods are disclosed. The devices can be used as or to support colonoscopies or endoscopes. The devices can have longitudinally extensible cells that can be selectively inflated. The devices can have articulable links. The devices can be removably attached to elongated elements, such as colonoscopes or other endoscopes.

12 Claims, 24 Drawing Sheets

Related U.S. Application Data

(60) Provisional application No. 60/887,319, filed on Jan. 30, 2007, provisional application No. 60/887,323, filed on Jan. 30, 2007, provisional application No. 60/949,219, filed on Jul. 11, 2007.

(51) Int. Cl.
*A61B 1/008* (2006.01)
*A61B 1/01* (2006.01)
*A61B 1/31* (2006.01)
*A61B 17/00* (2006.01)
*A61M 25/01* (2006.01)

(52) U.S. Cl.
CPC ........ *A61B 1/0055* (2013.01); *A61B 1/00071* (2013.01); *A61B 1/00135* (2013.01); *A61B 1/00151* (2013.01); *A61B 1/01* (2013.01); *A61B 1/31* (2013.01); *A61M 25/0113* (2013.01); *A61M 25/0116* (2013.01); *A61M 25/0133* (2013.01); *A61B 2017/003* (2013.01)

(58) Field of Classification Search
CPC .... A61B 2018/00196; A61M 25/0133; A61M 25/0136; A61M 25/0138; A61M 25/0144; A61M 25/0147; A61M 25/0141; A61M 25/0152; A61M 25/0155; A61M 25/0113; A61M 25/0116
USPC ........ 600/104, 106, 114–116, 156, 139–152; 604/95.01–95.05
See application file for complete search history.

(56) References Cited

U.S. PATENT DOCUMENTS

| | | |
|---|---|---|
| 3,970,495 A | 7/1976 | Ashton et al. |
| 4,176,662 A | 12/1979 | Frazer |
| 4,321,915 A | 3/1982 | Leighton et al. |
| 4,327,736 A | 5/1982 | Inoue |
| 4,516,972 A | 5/1985 | Samson |
| 4,517,979 A | 5/1985 | Pecenka |
| 4,525,228 A | 6/1985 | Bowen |
| 4,553,959 A | 11/1985 | Hickey et al. |
| 4,563,171 A | 1/1986 | Bodicky |
| 4,637,396 A | 1/1987 | Cook |
| 4,702,252 A | 10/1987 | Brooks et al. |
| 4,706,670 A | 11/1987 | Andersen et al. |
| 4,737,153 A | 4/1988 | Shimamura et al. |
| 4,779,611 A | 10/1988 | Grooters et al. |
| 4,809,678 A | 3/1989 | Klein |
| 4,863,440 A | 9/1989 | Chin |
| 4,881,553 A | 11/1989 | Grossman |
| 4,894,281 A | 1/1990 | Yagi et al. |
| 4,952,357 A | 8/1990 | Euteneuer |
| 4,969,888 A | 11/1990 | Scholten et al. |
| 5,087,246 A | 2/1992 | Smith |
| 5,108,370 A | 4/1992 | Walinsky |
| 5,108,404 A | 4/1992 | Scholten et al. |
| 5,112,304 A | 5/1992 | Barlow et al. |
| 5,116,318 A | 5/1992 | Hillstead |
| 5,137,512 A | 8/1992 | Burns et al. |
| 5,147,302 A | 9/1992 | Euteneuer et al. |
| 5,163,949 A | 11/1992 | Bonutti |
| 5,181,911 A | 1/1993 | Shturman |
| 5,190,058 A | 3/1993 | Jones et al. |
| 5,191,879 A * | 3/1993 | Krauter .............. G02B 23/2484 359/823 |
| 5,192,296 A | 3/1993 | Bhate et al. |
| 5,201,706 A | 4/1993 | Noguchi et al. |
| 5,217,440 A | 6/1993 | Frassica |
| 5,226,880 A | 7/1993 | Martin |
| 5,226,888 A | 7/1993 | Arney |
| 5,236,423 A | 8/1993 | Mix et al. |
| 5,250,070 A | 10/1993 | Parodi |
| 5,259,364 A | 11/1993 | Bob et al. |
| 5,270,086 A | 12/1993 | Hamlin |
| 5,290,306 A | 3/1994 | Trotta et al. |
| 5,295,959 A | 3/1994 | Gurbel et al. |
| 5,295,995 A | 3/1994 | Kleiman |
| 5,304,340 A | 4/1994 | Downey |
| 5,308,356 A | 5/1994 | Blackshear, Jr. et al. |
| 5,318,587 A | 6/1994 | Davey |
| 5,325,846 A | 7/1994 | Szabo |
| 5,333,568 A | 8/1994 | Meldner et al. |
| 5,338,299 A | 8/1994 | Barlow |
| 5,342,301 A | 8/1994 | Saab |
| 5,350,361 A | 9/1994 | Tsukashima et al. |
| 5,378,237 A | 1/1995 | Boussignac et al. |
| 5,383,467 A | 1/1995 | Auer et al. |
| 5,383,856 A | 1/1995 | Bersin |
| 5,388,590 A | 2/1995 | Horrigan et al. |
| 5,398,670 A | 3/1995 | Ortiz et al. |
| 5,403,280 A | 4/1995 | Wang |
| 5,409,495 A | 4/1995 | Osborn |
| 5,417,707 A | 5/1995 | Parkola |
| 5,425,710 A | 6/1995 | Khair et al. |
| 5,433,706 A | 7/1995 | Abiuso |
| 5,458,572 A | 10/1995 | Campbell et al. |
| 5,470,314 A | 11/1995 | Walinsky |
| 5,496,276 A | 3/1996 | Wang et al. |
| 5,501,667 A | 3/1996 | Verduin, Jr. |
| 5,513,654 A | 5/1996 | Delson |
| 5,545,132 A | 8/1996 | Fagan et al. |
| 5,554,120 A | 9/1996 | Chen et al. |
| 5,556,382 A | 9/1996 | Adams |
| 5,556,389 A | 9/1996 | Liprie |
| 5,556,911 A | 9/1996 | Walther et al. |
| 5,558,642 A | 9/1996 | Schweich, Jr. et al. |
| 5,575,771 A | 11/1996 | Walinsky |
| 5,586,968 A | 12/1996 | Grundl et al. |
| 5,587,125 A | 12/1996 | Roychowdhury |
| 5,591,129 A | 1/1997 | Shoup et al. |
| 5,599,306 A | 2/1997 | Klein et al. |
| 5,609,606 A | 3/1997 | O'Boyle |
| 5,645,529 A | 7/1997 | Fagan et al. |
| 5,647,848 A | 7/1997 | Jergensen |
| 5,653,697 A | 8/1997 | Quiachon et al. |
| 5,662,587 A | 9/1997 | Grundfest et al. |
| 5,669,879 A | 9/1997 | Duer |
| 5,669,920 A | 9/1997 | Conley et al. |
| 5,702,373 A | 12/1997 | Samson |
| 5,713,867 A | 2/1998 | Morris |
| 5,718,684 A | 2/1998 | Gupta |
| 5,749,851 A | 5/1998 | Wang |
| 5,749,852 A | 5/1998 | Schwab et al. |
| 5,759,172 A | 6/1998 | Weber et al. |
| 5,763,519 A | 6/1998 | Springsteen |
| 5,792,300 A | 8/1998 | Inderbitzen et al. |
| 5,797,877 A | 8/1998 | Hamilton et al. |
| 5,819,736 A | 10/1998 | Avny et al. |
| 5,827,289 A | 10/1998 | Reiley et al. |
| 5,830,181 A | 11/1998 | Thornton |
| 5,840,064 A | 11/1998 | Liprie |
| 5,865,801 A | 2/1999 | Houser |
| 5,868,779 A | 2/1999 | Ruiz |
| 5,873,880 A | 2/1999 | Williams et al. |
| 5,897,488 A | 4/1999 | Ueda |
| 5,947,924 A | 9/1999 | Liprie |
| 5,951,458 A | 9/1999 | Hastings et al. |
| 5,968,012 A * | 10/1999 | Ren et al. .................. 604/96.01 |
| 5,968,013 A | 10/1999 | Smith et al. |
| 5,972,015 A | 10/1999 | Scribner et al. |
| 6,015,421 A | 1/2000 | Echeverry et al. |
| 6,036,697 A | 3/2000 | Dicaprio |
| 6,048,346 A | 4/2000 | Reiley et al. |
| 6,056,837 A | 5/2000 | Lieber et al. |
| 6,066,154 A | 5/2000 | Reiley et al. |
| 6,099,454 A | 8/2000 | Hastings et al. |
| 6,123,080 A | 9/2000 | Mohan et al. |
| 6,124,007 A | 9/2000 | Wang et al. |
| 6,143,015 A | 11/2000 | Nobles |
| 6,156,254 A | 12/2000 | Andrews et al. |
| 6,165,163 A | 12/2000 | Chien et al. |

(56) References Cited

U.S. PATENT DOCUMENTS

| | | | |
|---|---|---|---|
| 6,183,492 B1 | 2/2001 | Hart et al. | |
| 6,184,923 B1 * | 2/2001 | Miyazaki | A61B 1/00096 348/75 |
| 6,190,357 B1 | 2/2001 | Ferrari et al. | |
| 6,234,951 B1 | 5/2001 | Hastings | |
| 6,235,043 B1 | 5/2001 | Reiley et al. | |
| 6,241,734 B1 | 6/2001 | Scribner et al. | |
| 6,242,063 B1 | 6/2001 | Ferrera et al. | |
| 6,248,110 B1 | 6/2001 | Reiley et al. | |
| 6,284,333 B1 | 9/2001 | Wang et al. | |
| 6,286,555 B1 | 9/2001 | Pauker et al. | |
| 6,346,072 B1 | 2/2002 | Cooper | |
| 6,358,199 B1 * | 3/2002 | Pauker | A61M 25/0113 600/102 |
| 6,398,776 B1 | 6/2002 | Sekino et al. | |
| 6,447,444 B1 | 9/2002 | Avni et al. | |
| 6,450,988 B1 | 9/2002 | Bradshaw | |
| 6,465,067 B1 | 10/2002 | Wang et al. | |
| 6,488,653 B1 | 12/2002 | Lombardo | |
| 6,494,862 B1 | 12/2002 | Ray et al. | |
| 6,540,734 B1 | 4/2003 | Chiu et al. | |
| 6,540,778 B1 | 4/2003 | Quiachon et al. | |
| 6,554,820 B1 | 4/2003 | Wendlandt et al. | |
| 6,605,056 B2 | 8/2003 | Eidenschink et al. | |
| 6,610,083 B2 | 8/2003 | Keller et al. | |
| 6,623,504 B2 | 9/2003 | Vrba et al. | |
| 6,626,888 B1 | 9/2003 | Conway et al. | |
| 6,629,952 B1 | 10/2003 | Chien et al. | |
| 6,632,235 B2 | 10/2003 | Weikel et al. | |
| 6,645,213 B2 | 11/2003 | Sand et al. | |
| 6,651,659 B2 | 11/2003 | Izuchukwu | |
| 6,652,568 B1 | 11/2003 | Becker et al. | |
| 6,663,648 B1 | 12/2003 | Trotta | |
| 6,679,860 B2 | 1/2004 | Stiger | |
| 6,685,718 B1 | 2/2004 | Wyzgala et al. | |
| 6,695,809 B1 | 2/2004 | Lee | |
| 6,716,216 B1 | 4/2004 | Boucher et al. | |
| 6,719,773 B1 | 4/2004 | Boucher et al. | |
| 6,733,474 B2 | 5/2004 | Kusleika | |
| 6,746,425 B1 | 6/2004 | Beckham | |
| 6,752,829 B2 | 6/2004 | Kocur et al. | |
| 6,756,094 B1 | 6/2004 | Wang et al. | |
| 6,773,447 B2 | 8/2004 | Laguna | |
| 6,796,960 B2 | 9/2004 | Cioanta et al. | |
| 6,872,223 B2 | 3/2005 | Roberts et al. | |
| 6,875,170 B2 * | 4/2005 | Francois et al. | 600/141 |
| 6,878,329 B2 | 4/2005 | Blankenship et al. | |
| 6,905,743 B1 | 6/2005 | Chen et al. | |
| 6,908,428 B2 | 6/2005 | Aizenfeld et al. | |
| 6,911,038 B2 | 6/2005 | Mertens et al. | |
| 6,923,822 B2 | 8/2005 | Crawford et al. | |
| 6,923,827 B2 | 8/2005 | Campbell et al. | |
| 6,942,680 B2 | 9/2005 | Grayzel et al. | |
| 6,945,957 B2 | 9/2005 | Freyman | |
| 6,946,173 B2 | 9/2005 | Lim et al. | |
| 6,951,675 B2 | 10/2005 | Chin et al. | |
| 6,966,889 B2 | 11/2005 | Saab | |
| 6,977,103 B2 | 12/2005 | Chen et al. | |
| 6,979,341 B2 | 12/2005 | Scribner et al. | |
| 7,011,646 B2 | 3/2006 | Blankenship | |
| 7,029,732 B2 | 4/2006 | Wang et al. | |
| 7,037,562 B2 | 5/2006 | Jimenez | |
| 7,044,954 B2 | 5/2006 | Reiley et al. | |
| 7,052,507 B2 | 5/2006 | Wakuda et al. | |
| 7,081,096 B2 | 7/2006 | Brister et al. | |
| 7,153,306 B2 | 12/2006 | Ralph et al. | |
| 7,160,306 B2 | 1/2007 | Matsuzaki et al. | |
| 7,163,504 B1 | 1/2007 | Chiu et al. | |
| 7,166,121 B2 | 1/2007 | Reiley et al. | |
| 7,172,796 B2 | 2/2007 | Kinoshita et al. | |
| 7,252,605 B2 | 8/2007 | Snider | |
| 7,261,720 B2 | 8/2007 | Stevens et al. | |
| 7,273,471 B1 | 9/2007 | Wang et al. | |
| 7,279,208 B1 | 10/2007 | Goffena et al. | |
| 7,309,324 B2 | 12/2007 | Hayes et al. | |
| 7,320,704 B2 | 1/2008 | Lashinski et al. | |
| 7,335,184 B2 | 2/2008 | Laguna | |
| 7,384,411 B1 | 6/2008 | Condado | |
| 7,438,712 B2 | 10/2008 | Chouinard | |
| 7,481,803 B2 | 1/2009 | Kesten et al. | |
| 7,491,188 B2 | 2/2009 | Holman et al. | |
| 7,500,982 B2 | 3/2009 | Pepper | |
| 7,635,510 B2 | 12/2009 | Horn et al. | |
| 7,641,844 B2 | 1/2010 | Melsheimer | |
| 7,691,080 B2 | 4/2010 | Seward et al. | |
| 7,691,082 B2 | 4/2010 | Shippy, III et al. | |
| 7,753,875 B2 | 7/2010 | Burton | |
| 7,758,892 B1 | 7/2010 | Chen et al. | |
| 7,762,985 B2 | 7/2010 | Kabrick et al. | |
| 7,833,218 B2 | 11/2010 | Lunn et al. | |
| 7,850,811 B2 | 12/2010 | Hart et al. | |
| 7,879,053 B2 | 2/2011 | Trinidad | |
| 7,914,487 B2 | 3/2011 | Davies, Jr. et al. | |
| 7,914,503 B2 | 3/2011 | Goodson, IV et al. | |
| 7,942,847 B2 | 5/2011 | Stupecky et al. | |
| 7,967,798 B2 | 6/2011 | Reydel et al. | |
| 8,048,028 B2 | 11/2011 | Horn et al. | |
| 8,075,519 B2 | 12/2011 | Min et al. | |
| 8,122,809 B2 | 2/2012 | Simpson | |
| 8,153,181 B2 | 4/2012 | Holman et al. | |
| 8,187,297 B2 | 5/2012 | Makower et al. | |
| 8,206,332 B2 | 6/2012 | Noda et al. | |
| 8,221,484 B2 | 7/2012 | Wesselmann | |
| 2001/0043996 A1 | 11/2001 | Yamada et al. | |
| 2002/0026195 A1 | 2/2002 | Layne et al. | |
| 2002/0032371 A1 * | 3/2002 | Torii | A61B 1/0052 600/142 |
| 2002/0098307 A1 | 7/2002 | Schwartz et al. | |
| 2002/0161388 A1 | 10/2002 | Samuels et al. | |
| 2003/0078539 A1 | 4/2003 | Peterson et al. | |
| 2003/0105386 A1 * | 6/2003 | Voloshin et al. | 600/114 |
| 2003/0236495 A1 | 12/2003 | Kennedy | |
| 2004/0010263 A1 | 1/2004 | Boucher et al. | |
| 2004/0061261 A1 | 4/2004 | Gonzalez et al. | |
| 2004/0093058 A1 | 5/2004 | Cottone et al. | |
| 2004/0098017 A1 | 5/2004 | Saab et al. | |
| 2004/0098078 A1 | 5/2004 | Stoltze et al. | |
| 2004/0133197 A1 | 7/2004 | Utley et al. | |
| 2004/0143161 A1 | 7/2004 | Baror et al. | |
| 2004/0167561 A1 | 8/2004 | Boucher et al. | |
| 2004/0181252 A1 | 9/2004 | Boyle et al. | |
| 2004/0232589 A1 | 11/2004 | Kawabata et al. | |
| 2005/0008806 A1 | 1/2005 | Schewe et al. | |
| 2005/0021018 A1 | 1/2005 | Anderson et al. | |
| 2005/0082965 A1 | 4/2005 | Huang et al. | |
| 2005/0085693 A1 | 4/2005 | Belson et al. | |
| 2005/0090846 A1 | 4/2005 | Pedersen et al. | |
| 2005/0090852 A1 | 4/2005 | Layne et al. | |
| 2005/0123702 A1 | 6/2005 | Beckham | |
| 2005/0149022 A1 | 7/2005 | Shaolian et al. | |
| 2005/0209674 A1 | 9/2005 | Kutscher et al. | |
| 2005/0228224 A1 * | 10/2005 | Okada et al. | 600/104 |
| 2005/0228397 A1 | 10/2005 | Malandain et al. | |
| 2005/0234296 A1 * | 10/2005 | Saadat et al. | 600/129 |
| 2005/0271844 A1 | 12/2005 | Mapes et al. | |
| 2005/0277877 A1 | 12/2005 | Motsenbocker et al. | |
| 2005/0288434 A1 | 12/2005 | Sugiura et al. | |
| 2006/0015010 A1 | 1/2006 | Jaffe et al. | |
| 2006/0025844 A1 | 2/2006 | Majercak et al. | |
| 2006/0085023 A1 | 4/2006 | Davies, Jr. et al. | |
| 2006/0085024 A1 | 4/2006 | Pepper et al. | |
| 2006/0111611 A1 | 5/2006 | Eizenfeld et al. | |
| 2006/0130209 A1 | 6/2006 | Golan | |
| 2006/0149128 A1 | 7/2006 | Baror | |
| 2006/0149131 A1 | 7/2006 | Or | |
| 2006/0183974 A1 | 8/2006 | Levy et al. | |
| 2006/0195005 A1 | 8/2006 | Sakai | |
| 2006/0195135 A1 | 8/2006 | Ayoub | |
| 2006/0224113 A1 | 10/2006 | Van Sloten et al. | |
| 2006/0235368 A1 | 10/2006 | Oz | |
| 2006/0235458 A1 | 10/2006 | Belson | |
| 2006/0252989 A1 | 11/2006 | Or et al. | |
| 2006/0271093 A1 | 11/2006 | Holman et al. | |
| 2006/0271844 A1 | 11/2006 | Suklikar et al. | |

(56) References Cited

U.S. PATENT DOCUMENTS

| | | |
|---|---|---|
| 2007/0010844 A1 | 1/2007 | Gong et al. |
| 2007/0010865 A1 | 1/2007 | Dann et al. |
| 2007/0016133 A1 | 1/2007 | Pepper |
| 2007/0021772 A1 | 1/2007 | Von Oepen et al. |
| 2007/0038178 A1 | 2/2007 | Kusleika |
| 2007/0043262 A1 | 2/2007 | Levy et al. |
| 2007/0100279 A1 | 5/2007 | Bates |
| 2007/0106216 A1 | 5/2007 | Noddin |
| 2007/0112250 A1 | 5/2007 | Kura et al. |
| 2007/0112300 A1 | 5/2007 | Roman et al. |
| 2007/0118143 A1 | 5/2007 | Ralph et al. |
| 2007/0207186 A1 | 9/2007 | Scanlon et al. |
| 2007/0213591 A1 | 9/2007 | Aizenfeld et al. |
| 2007/0225800 A1 | 9/2007 | Sahatjian et al. |
| 2007/0244501 A1 | 10/2007 | Horn et al. |
| 2007/0250101 A1 | 10/2007 | Horn et al. |
| 2007/0255206 A1 | 11/2007 | Reneker et al. |
| 2007/0265565 A1 | 11/2007 | Johnson |
| 2007/0267128 A1 | 11/2007 | Horn et al. |
| 2007/0270688 A1 | 11/2007 | Gelbart et al. |
| 2007/0286982 A1 | 12/2007 | Higgins et al. |
| 2008/0033477 A1 | 2/2008 | Campbell et al. |
| 2008/0086133 A1 | 4/2008 | Kuslich et al. |
| 2008/0087431 A1 | 4/2008 | Willauer et al. |
| 2008/0097300 A1 | 4/2008 | Eskaros et al. |
| 2008/0097301 A1 | 4/2008 | Alpini et al. |
| 2008/0097374 A1 | 4/2008 | Korleski et al. |
| 2008/0140173 A1 | 6/2008 | Eskaros et al. |
| 2008/0183038 A1 | 7/2008 | Tilson et al. |
| 2008/0228139 A1 | 9/2008 | Melsheimer et al. |
| 2008/0255512 A1 | 10/2008 | Krivoruchko |
| 2008/0287961 A1* | 11/2008 | Miyamoto ......... A61B 1/00098 606/127 |
| 2009/0012500 A1 | 1/2009 | Murata et al. |
| 2009/0038752 A1 | 2/2009 | Weng et al. |
| 2009/0043254 A1 | 2/2009 | Pepper et al. |
| 2009/0099517 A1 | 4/2009 | Steadham |
| 2009/0294031 A1 | 12/2009 | Pepper et al. |
| 2009/0299327 A1 | 12/2009 | Tilson et al. |
| 2009/0299374 A1 | 12/2009 | Tilson et al. |
| 2009/0299401 A1 | 12/2009 | Tilson |
| 2009/0301643 A1 | 12/2009 | Tilson et al. |
| 2009/0306589 A1 | 12/2009 | Tilson et al. |
| 2009/0318861 A1 | 12/2009 | Corcoran et al. |
| 2010/0023047 A1 | 1/2010 | Simpson |
| 2010/0049123 A1 | 2/2010 | Alpini et al. |
| 2010/0076437 A1 | 3/2010 | Tilson et al. |
| 2010/0114022 A1 | 5/2010 | Hirszowicz et al. |
| 2010/0152654 A1 | 6/2010 | Tilson et al. |
| 2010/0179581 A1 | 7/2010 | Beckham |
| 2010/0198016 A1 | 8/2010 | Tilson et al. |
| 2010/0241152 A1 | 9/2010 | Tilson et al. |
| 2010/0241153 A1 | 9/2010 | Tilson et al. |
| 2010/0241178 A1 | 9/2010 | Tilson et al. |
| 2010/0243135 A1 | 9/2010 | Pepper et al. |
| 2011/0060186 A1 | 3/2011 | Tilson et al. |
| 2011/0087070 A1 | 4/2011 | Tilson et al. |
| 2011/0144688 A1 | 6/2011 | Reiss et al. |
| 2011/0198019 A1 | 8/2011 | Tilson et al. |
| 2012/0179162 A1 | 7/2012 | Tilson et al. |

FOREIGN PATENT DOCUMENTS

| | | |
|---|---|---|
| EP | 0338557 A2 | 10/1989 |
| EP | 0425692 B1 | 5/1991 |
| EP | 0331040 B1 | 12/1991 |
| EP | 1103224 A1 | 5/2001 |
| EP | 0745547 B1 | 9/2002 |
| EP | 1036539 A1 | 10/2003 |
| EP | 0959937 B1 | 11/2003 |
| EP | 1083866 B1 | 10/2004 |
| EP | 1272131 B1 | 3/2006 |
| EP | 1294323 B1 | 4/2007 |
| EP | 1768737 | 4/2007 |
| EP | 1814477 | 8/2007 |
| EP | 1814625 | 8/2007 |
| EP | 1865867 | 12/2007 |
| EP | 1303236 B1 | 12/2008 |
| EP | 0987991 B1 | 4/2009 |
| EP | 1073371 B2 | 7/2009 |
| EP | 1328203 B1 | 11/2009 |
| EP | 1083836 B1 | 10/2010 |
| EP | 1272113 B1 | 3/2012 |
| FR | 2742652 A1 | 6/1997 |
| GB | 1566674 A | 5/1980 |
| GB | 2130093 A | 5/1984 |
| GB | 2231231 A | 11/1990 |
| GB | 2306111 A | 4/1997 |
| JP | 07-000934 | 1/1995 |
| JP | 10-277157 | 10/1998 |
| JP | 2003-117002 | 4/2003 |
| WO | WO86/06944 A1 | 12/1986 |
| WO | WO87/00442 A1 | 1/1987 |
| WO | WO95/08965 A1 | 4/1995 |
| WO | WO95/09667 A1 | 4/1995 |
| WO | WO95/18647 A2 | 7/1995 |
| WO | WO95/20362 A1 | 8/1995 |
| WO | WO96/39970 A1 | 12/1996 |
| WO | WO97/32515 A1 | 9/1997 |
| WO | WO99/13331 A1 | 3/1999 |
| WO | WO00/12169 A1 | 3/2000 |
| WO | WO00/44275 A1 | 8/2000 |
| WO | WO02/30484 A2 | 4/2002 |
| WO | WO03/022165 A1 | 3/2003 |
| WO | WO03/059214 A2 | 7/2003 |
| WO | WO03/082363 A1 | 10/2003 |
| WO | WO2005/025648 A2 | 3/2005 |
| WO | WO2005/072804 A1 | 8/2005 |
| WO | WO2006/016299 A1 | 2/2006 |
| WO | WO2006/034396 A2 | 3/2006 |
| WO | WO2008/076992 A2 | 6/2008 |
| WO | WO2009/040610 A1 | 4/2009 |
| WO | WO2009/052838 A1 | 4/2009 |

OTHER PUBLICATIONS

Matasov et al.; Morphological changes in the intestine in its intubation in experiment (in Russian with English Summary); Khirurgiia (Mosk); No. 10; pp. 42-44; Oct. 1982.

Swain; Colonoscopy: New designs for the future; Gastrointest Endoscopy Clin N Am; 15(4); pp. 839-863; Oct. 2005.

Tremco; BURmastic® Supreme Composite Ply; Product Information; 2 pgs.; Jul. 2002.

Tilson et al.; U.S. Appl. No. 13/810,153 entitled "Inflatable Medical Devices," filed Mar. 20, 2013.

\* cited by examiner

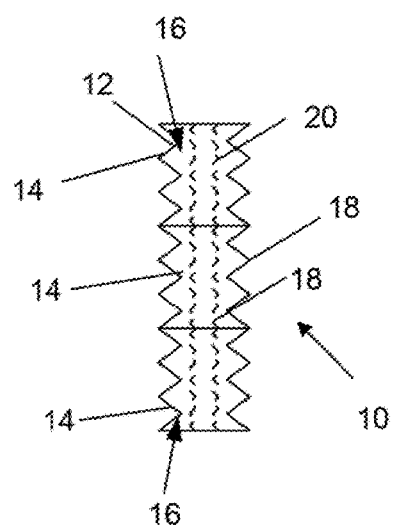
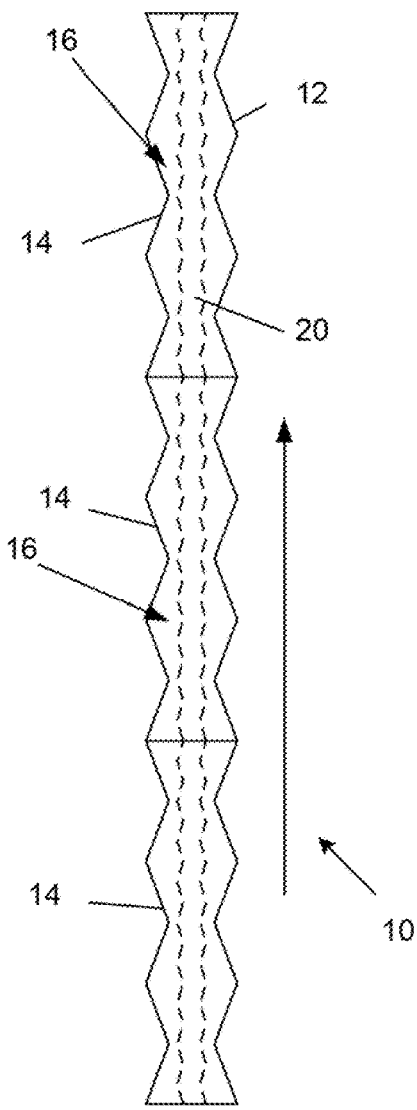
Fig. 1
Fig. 2

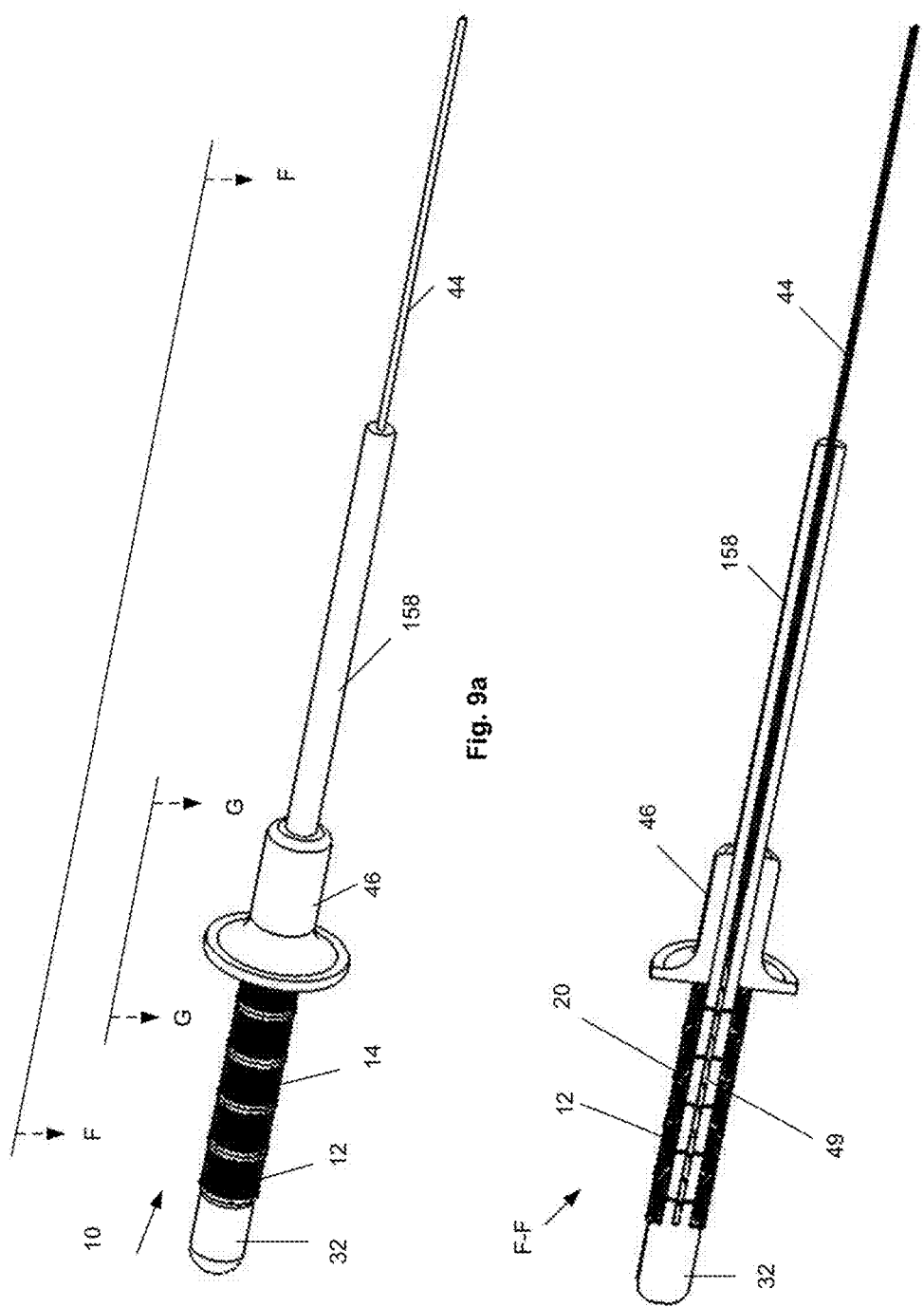

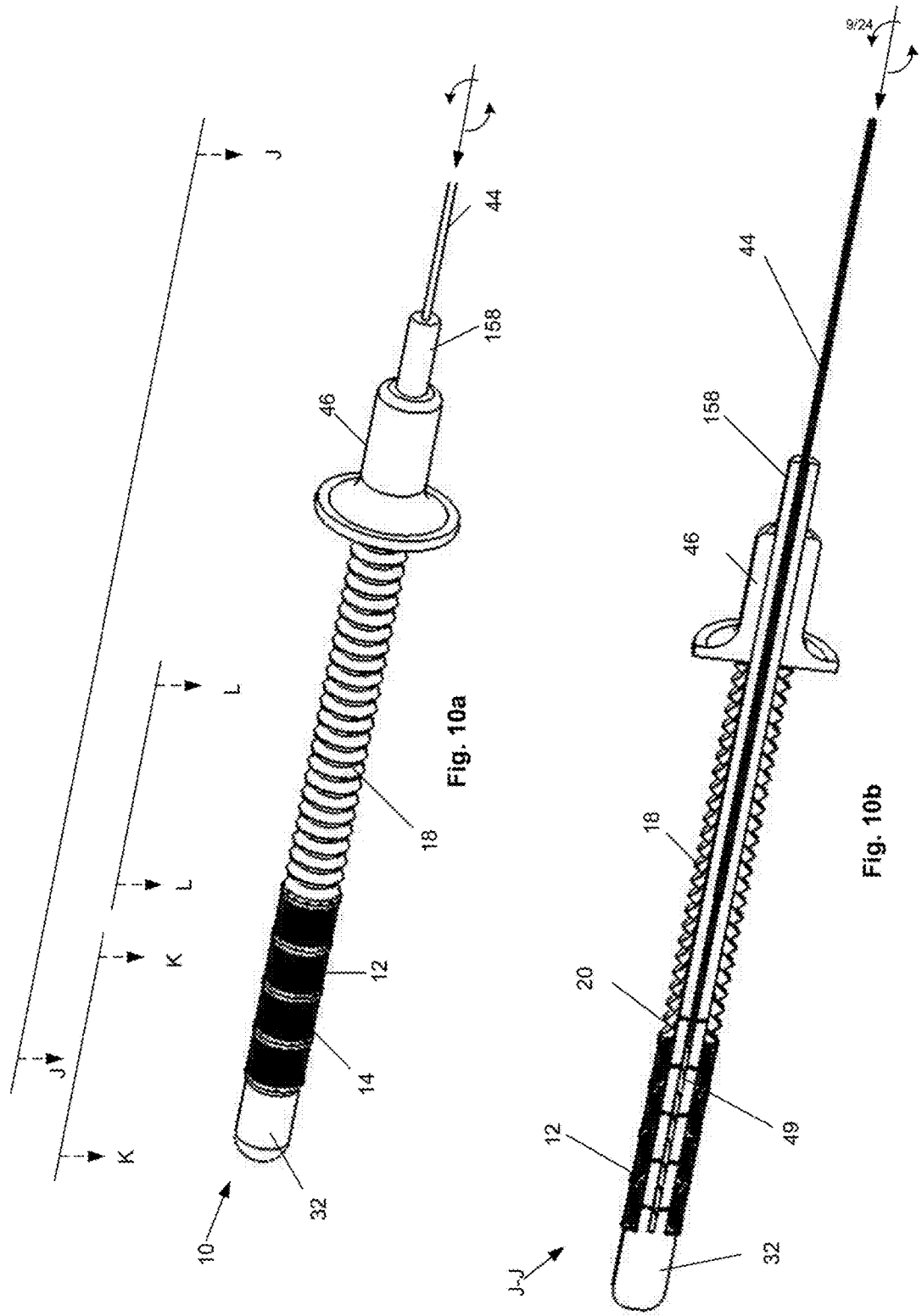

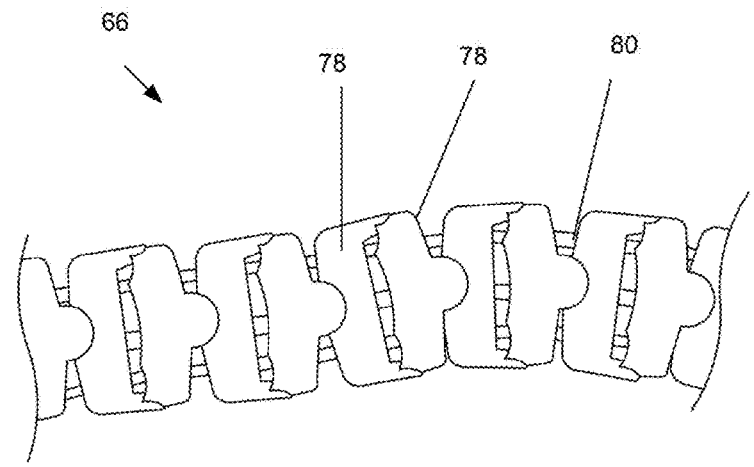
Fig. 12
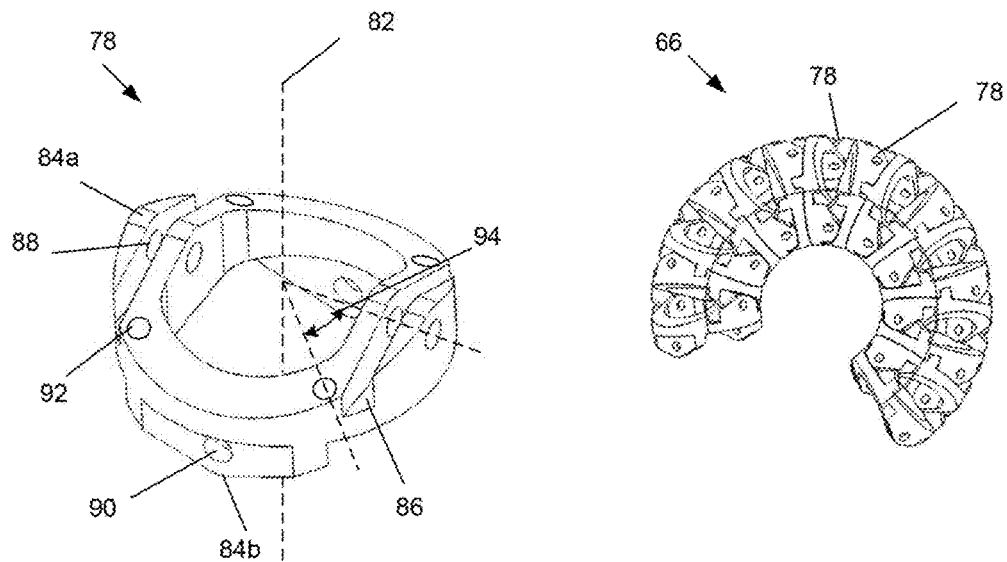
Fig. 13
Fig. 14

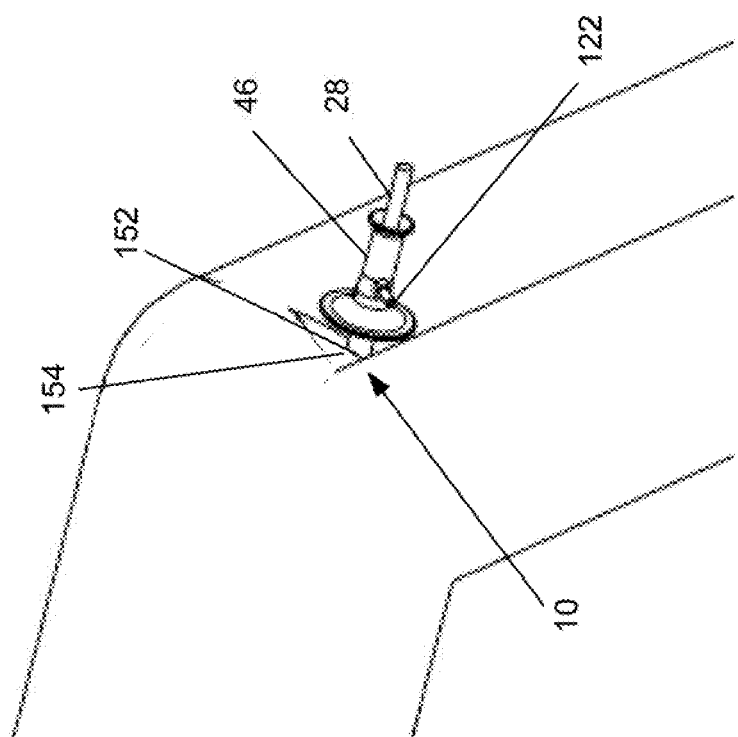

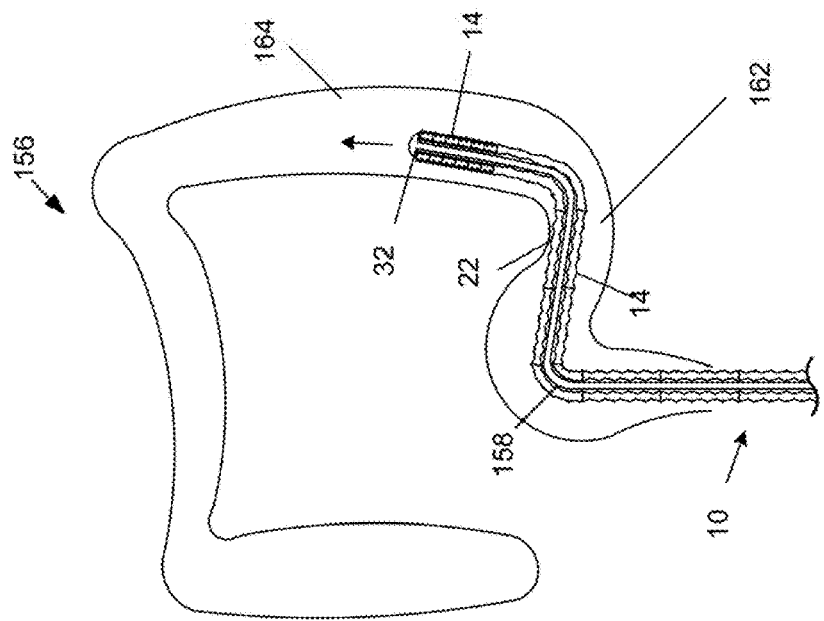
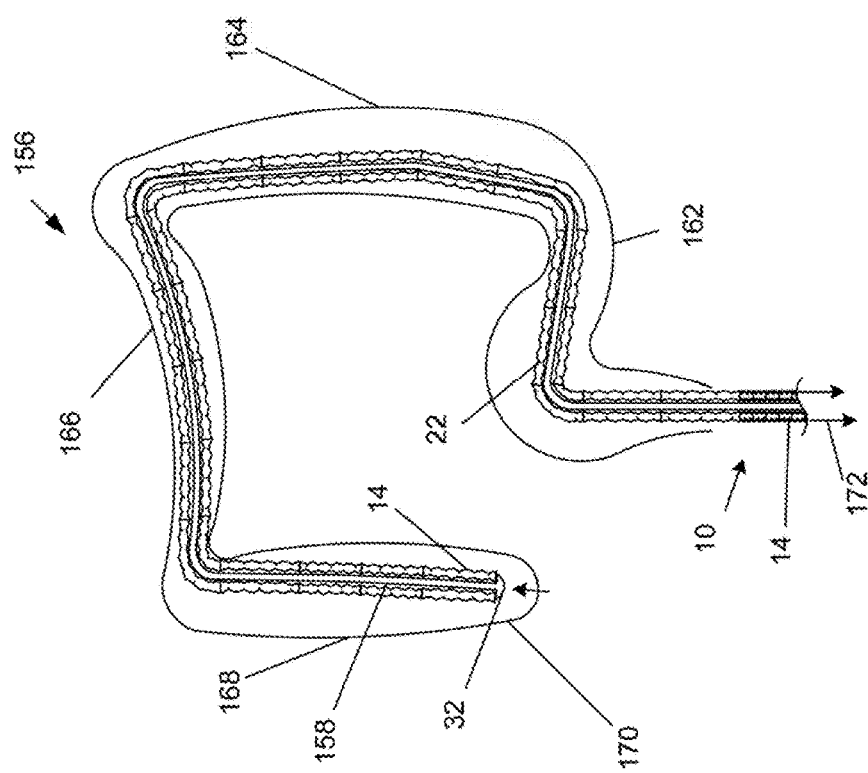

BIOLOGICAL NAVIGATION DEVICE

CROSS-REFERENCE TO RELATED APPLICATIONS

This application is a continuation of prior PCT Application No. PCT/US2008/052542, which claims priority to U.S. Provisional Application Ser. Nos. 60/887,319, filed 30 Jan. 2007; 60/887,323, filed 30 Jan. 2007; and 60/949,219, filed 11 Jul. 2007, which are all incorporated herein by reference in their entireties.

BACKGROUND OF THE INVENTION

1. Field of the Invention

The presented invention relates generally to devices for the exploration of luminal cavities. One such device example is an endoscope, which can be used to explore body passages. Such passages typically include, but are not limited to, the GI tract, the pulmonary and gynecological systems, urological tracts, and the coronary vasculature. One application is directed towards the exploration of the lower part of the GI tract, for example the large intestine or colon.

2. Description of the Related Art

Colonoscopy is a diagnostic and sometimes therapeutic procedure used in the prevention, diagnosis and treatment of colon cancer, among other pathologies. With colonoscopy, polyps can be harvested before they metastasize and spread. With regular colonoscopies, the incidence of colon cancer can be substantially reduced.

The anus can provide entry into the colon for a colonoscopy. The colon extends from the rectum to the cecum and has sigmoid, descending, transverse and ascending portions. The sigmoid colon is the s-shaped portion of the colon between the descending colon and the rectum.

Colonoscopy typically involves the anal insertion of a semi-flexible shaft. To typically navigate the colon, the forward few inches of tip are flexed or articulated as the shaft is alternately pushed, pulled, and twisted in a highly skill-based attempt to advance to the end of the colon: the cecum. The medical professional imparts these motions in close proximity to the anus, where the device enters. Tip flexure has typically been accomplished by rotating wheels one that controls cables that move the tip right-left, and one that controls cables that move the tip up-down.

Colonoscopes typically utilize various conduits or channels. The conduits or channels often contain elements that enable vision (e.g., fiber optics, CCD cameras, CMOS camera chips) and lighting (e.g., fiber optic light sources, high power LEDs (Light Emitting Diodes)). They have conduits that provide suction or pressurization, fluid irrigation, the delivery of instruments (e.g., for cutting, coagulation, polyp removal, tissue sampling) and lens cleaning elements (typically a right angle orifice that exits near the camera, such that a fluid flush provides a cleansing wash).

Colonoscopes include articulating sections at their tip, which allow the user to position the tip. These articulating sections have rigid link bodies that rotate relative to each other through the use of pins at their connecting joints. As tensile cables pull from the periphery of the articulating sections, they impart torques, which rotate the link sections on their pins, articulating the tip section. The links are usually rotated by two or four tensile cables.

Typical commercially available colonoscopes are currently reusable. However, as disposable and other lower-cost colonoscopes are developed, these articulatable sections are no longer practical. Their high part count creates total costs that are exorbitant for a lower cost, disposable device. The pivot pins can also fall out, which can create a patient danger. Their design geometries, while suited for long life, high cost, high strength metals elements, don't readily suit themselves to the design goals of lower-cost and more readily mass-produced parts.

Suction can be utilized to remove debris or fluid. The colon can be pressurized to reconfigure the colon into an expanded cross-section to enhance visualization.

During advancement of the colonoscope through the colon, landmarks are noted and an attempt is made to visualize a significant portion of the colon's inside wall. Therapeutic actions can occur at any time, but are typically performed during withdrawal.

Navigating the long, small diameter colonoscope shaft in compression through the colon—a circuitous route with highly irregular anatomy—can be very difficult. Studies have shown a learning curve for doctors performing colonoscopies of greater than two-hundred cases. Even with the achievement of such a practice milestone, the cecum is often not reached, thereby denying the patient the potential for a full diagnosis.

During colonoscopy, significant patient pain can result. This is typically not the result of colon wall contact or of anal entry. The primary cause of pain is thought to be stretching and gross distortion of the mesocolon (the mesentery that attaches the colon to other internal organs). This is commonly referred to as 'looping' and is a result of trying to push a long, small diameter shaft in compression as the clinician attempts to navigate a torturous colon. While attempting to advance the tip by pushing on the scope, often all that occurs is that intermediate locations are significantly stretched and grossly distorted. Due to this pain, various forms of anesthesia are typically given to the patient. Anesthesia delivery results in the direct cost of the anesthesia, the cost to professionally administer, the costs associated with the capital equipment and its facility layouts, and the costs associated with longer procedure time (e.g., prep, aesthesia administration, post-procedure monitoring, and the need to have someone else drive the patient home). It has been estimated that forty percent of the cost of a colonoscopy can be attributed to the procedure's need for anesthesia.

Cleaning of colonoscopes is also an issue. Cleaning is time consuming, and lack of cleaning can result in disease transmission. Cleaning can utilize noxious chemicals and requires back-up scopes (some in use while others being cleaned). Cleaning also creates significant wear-and-tear of the device, which can lead to the need for more servicing.

It would therefore be desirable to create a system that is less painful—possibly not even requiring anesthesia—is significantly easier to use, and does not require cleaning.

Everting tube systems have been proposed for use as colonoscopes. However, multiple challenges exist for everting systems. One typical challenge is the differential speed between the center lumen and the tip. For example, as the typical everting tube is advanced, the center lumen of the colonoscope advances 2" for every 1" of eversion front advancement. When the center advances it moves only itself, whereas tip movement advances material on both sides. Because there is this dual wall material requirement for tip advancement, two times as much material is required, so it inherently must travel at half the rate.

Anything that is in the center of the typical everting tube is 'pressure clamped,' as the tube's inner diameter collapses to no cross sectional area as the tube is pressurized. This can make it difficult to try to solve the 2:1 problem in a typical everting tube by sliding elements in the inner diameter or central region.

This 2:1 advancement issue and the pressure clamping can make it difficult to locate traditional colonoscope tip elements at the everting tip's leading edge. Given that the tube is often long and pressurized, it therefore often precludes the ability to create a functioning center working channel.

Another issue is internal drag. Material (e.g., tube wall) fed to the tip can cause increased capstan drag, for, example the overall system advance force can be retarded to the point of stopping extension.

Optimal material selection is a highly significant challenge. The desired structure must have a rare combination of features: softness, strength, radial stiffness, low thickness, freedom from leaks, flex-crack resistance, puncture resistance, appropriate coefficient of friction, the potential for modifiable geometry as a function of length, and appropriate manufacturability and cost. Monolithic materials have proven insufficient at providing the variety of requisite specifications.

It can be difficult to create a system that is of adequately low stiffness. Larger diameters create higher propulsive forces, but they also do not typically readily conform to the colon in a lumen-centric manner and can be overly stiff.

Historically, several solutions have been suggested. One involves periodically depressurizing the system then withdrawing elements so that their leading edges match. This is time consuming and creates an undesirably non-continuous and geometrically interrupted procedure. It is also very difficult to create 'correct' undesirable relative motion to a deflated structure that essentially is no longer a structure. Another approach involves driving the inner lumen (typically with a special, thicker, anti-buckle wall). Because it is driven in compression rather than through pressure, the everting front can be inflated to a lower pressure such that its pressure clamping forces are less significant. This approach, augmented by the significant infusion of liberal amounts of interluminal lubricants, should enable advance. However, it has yet to be commercialized, it is very complicated, creates an undesirably larger diameter instrument, has lubrication leakage issues, and breaks down at longer advance lengths.

Additionally, colonoscopic devices have found it notably challenging to create methods to steer through torturous geometries, particularly without undue colon wall stresses and subsequent mesocolon stretch. Steering kinematics have been an ongoing challenge—certainly for existing colonoscopes (which result in 'looping'), but also to more effective next-generation devices.

Numerous driven tubes have been proposed for colonoscopy. Some utilize tube inlaid elements driven in compression. Others utilize tubes that are pressure driven, with their tubes being of multiple varieties, including the bellows variety, or everting types, or other stored material varieties, including scrunch, fold, or spooled versions.

The systems proposed to-date have geometries that create suboptimal steering efficacies. When a tube section's leading edge then has a steering section more distal, with typically a camera, lighting source, and working channel exit at the tip, the steering is less than effective when going around a corner: a situation is created in which the tip is retroflexed and is pointing in one desired direction of advance, but the system's advance is in an exactly opposite direction. The driven section presumes a vector—typically an axial manner—with the steering tip only having efficacy as it relates to its interaction with luminal walls. In a colonoscopy, this wall interaction is undesirable—it creates unnecessary wall stress and trauma, and can be a significant contributor to gross wall distortion, known as looping.

It would therefore be desirable to have system designs that enable more lumen-centric steering as the unit is advanced through colon curvature. Other improvements are also desired.

SUMMARY OF THE INVENTION

A device for navigating biological anatomy, such as a biological lumen, for example the GI tract, is disclosed. The device can be used for treatment and/or diagnosis. For example, the device can have a visualization element and can be used as a colonoscope and/or an endoscope. The device can also have a biopsy element. The device can also resect tissue and/or deliver drugs or other agents.

The device can have one or more pressure tubes. The pressure tube can have wide medical applicability, including, but not limited to, endoscopy and the dilation of anatomical structures.

The tubes can have a series of individual pressure cells. The cells can each have one or more inflatable bladders. The bladder can be a separate bladder within the cell or substantially concurrent with the cell itself. The bladder can be a volume configured to receive and exhaust fluid pressure. The bladder can have a separate cover (e.g., a bag) within the cell. The cells can have expandable bellows. The cells can have substantially rigid end plates with flexible (e.g., cloth or film-like) walls. As the cells are inflated, the device can be sequentially (i.e., cell by cell) advanced or reversed through the anatomy. The cells can be naturally fully-extended. The cells can be compressible to minimized length by applying a vacuum to the bladders of the cell. When the vacuum is released, the cells can be expanded to a full-length configuration with a minimal pressure (e.g., due to a natural resilient expansion of the cell). The minimal pressure requirement can keep structural requirements low for the cell, as well as keeping the device stiffness low. Once extended, the drag of the device against the lumen wall can be high enough to anchor the device to the lumen wall or other surrounding anatomy, for example such that the device would not move backwards as the distal tip is pushed forward.

The device can have an endoscopic tool articulating section that can have pins that are integral to the link bodies. The device can have articulating mechanisms that are low cost, high strength, low friction, of low part count, and of readily modifiable geometry. The components can be made of a wide range of materials, for example; injection molded from plastics.

The device can have a reciprocatable section, for example a reciprocating distal end of the device. The reciprocating section can be translated back and forth with respect to the remainder of the device. This reciprocating feature can enable the tip and its associated elements to move back and forth without the remainder of the colonoscope moving.

The device can also have a reciprocating section that can be steered in any direction and advanced. The remainder of the device can then be pulled forward internal to the device, thus advancing the device through the biological anatomy.

The development of disposable colonoscopes can reduce or eliminate cleaning costs, cleaning trouble, and the risk inherent to reused devices. The colonoscope can also be maximally effective because its use has not been compromised by previous cases and their inherent stress and wear.

Risks that can be reduced include the risk of poorly cleaned scopes, and the compromised device efficacy and reliability issues that are inherent to a field-contaminated high frequency use and reuse system.

The disclosed system, device or elements thereof can be used as elements that are combined into dedicated systems, as portions of dedicated systems (portions that can be reusable and portions that can be separable on a case-by-case basis, with some reused and some disposed of, sometimes referred to as 'semisposables' or 'resposables'), or as additive elements to existing systems (i.e., retrofit devices). Disposable systems can only need to function for limited life, and they do not have to interface with other components again and again. Semisposable varieties can utilize a very high-quality, higher-cost core device portion, and lower cost, single-use portions. The single use portions can negate the need for most of the typical cleaning, for example for the sheath exposed portions. Adding to existing systems can leverage large installed bases, methods, and usage patterns.

The device can also be used for interventional cardiology, for example for lesion dilation, as a stand-alone procedure, for pre-stent deployment ('pre-dil'), for post-stent deployment, as part of a stent-expansion inflatable structure used as a stent delivery system, or combinations thereof.

SUMMARY OF THE FIGURES

FIG. 1 illustrates a variation of the biological navigation device in a longitudinally contracted configuration.

FIG. 2 illustrates the biological navigation device of FIG. 1 in a longitudinally extended configuration.

FIG. 9a illustrates a variation of the biological navigation device and the elongated element in a longitudinally contracted configuration.

FIG. 9b illustrates a variation of cross-section F-F of FIG. 9a.

FIG. 9c illustrates a variation of cross-section G-G of FIG. 9a.

FIG. 10a illustrates a variation of the biological navigation device and the elongated element in a longitudinally partially-expanded configuration.

FIG. 10b illustrates a variation of cross-section J-J of FIG. 10a.

FIG. 10c illustrates a variation of cross-section K-K of FIG. 10a.

FIG. 12 illustrates a variation of the articulatable section of the biological navigation device.

FIG. 13 illustrates a variation of the link.

FIG. 14 illustrates a variation of the articulatable section having the links of FIG. 13.

FIG. 26 illustrates a method for using the biological navigation device in a patient.

FIGS. 27a through 27g illustrate a variation of a method for using the biological navigation device.

FIG. 27h illustrates a variation of a method for using the biological navigation device.

DETAILED DESCRIPTION

Figure 3C:
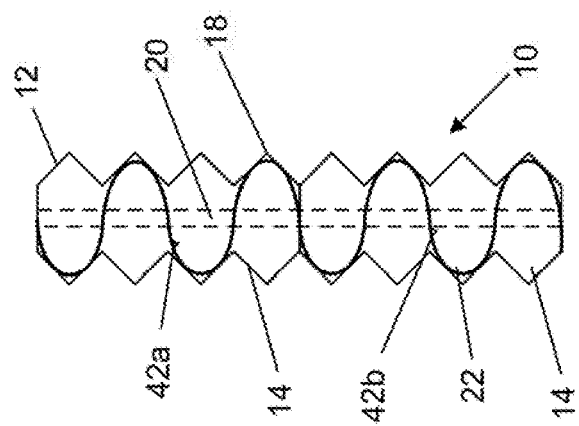
FIGS. 3a though 3c illustrate variations of the biological navigation device.

FIG. 1 illustrates a biological navigation device 10. The device can be used for navigation through a biological anatomy, such as a biological lumen, for example any or all of the GI tract (e.g., colon, stomach, esophagus) or cardiovascular vessels (e.g., arteries, veins, heart chambers).

The navigation device can be removably attached or integrated (e.g., permanently fixed, welded, glued, fused) with an elongated element 28. The elongated element 28 can be, for example, an endoscope or colonoscope. For example, the elongated element 28 can be a CF-Q160 series, PCF-160 series, or CF-2T160 series colonoscope (from Olympus America, Inc., Center Valley, Pa.), a Pentax EC-series colonoscope (from Pentax of America, Inc., Montvale, N.J.), a Fujinon HD Super CCD colonoscope, or a G-5 endoscope (from Fujinon Inc., Wayne, N.J.).

The device can have a longitudinally expandable tube 12 having one or more longitudinally extensible or extendable cells 14. Each cell 14 can have one or more fluid-tight bladders 16. The bladders 16 can be individually inflatable and deflatable, making the cells 14 individually inflatable (e.g., longitudinally expandable) and deflatable (e.g., longitudinally contractable).

The cells 14 can have one or more bellows 18 on the outer walls. The bellows 18 can be longitudinally expandable. The device can have a tool channel 20. The tool channel 20 can pass longitudinally through the center of the device. The tool channel 20 can have elastic and/or bellowed walls.

The tube 12 can have an engineered coefficient of friction (COF) on both its inner and outer surfaces.

The tube 12 can have a tube length. The tube length can be about 1.0 m (40 in.) to about 2.0 m (79 in.), for example about 1.6 m (63 in.). The tube 12 can have a tube outer diameter. The tube outer diameter can be from about 18 mm (0.71 in.) to about 23 mm (0.91 in.).

FIG. 2 illustrates that the cells 14 can be inflated (e.g., via inflating the bladders 16). The device can longitudinally expand, as shown by arrow.

Figure 3B:
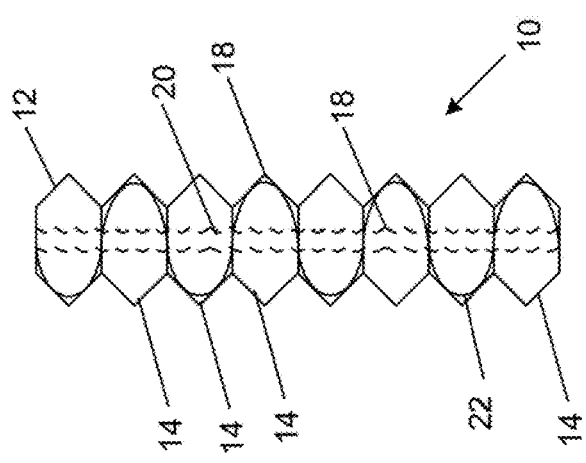
Figure 3A:
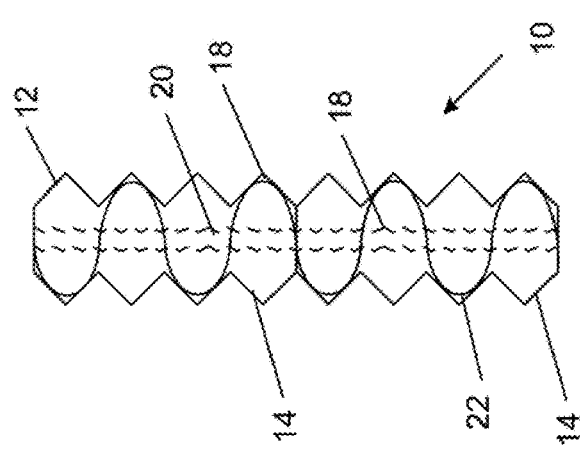

FIG. 3a illustrates that the device can have a control coil 22 inside or outside the cells 14. The control coil 22 can have one or more fluid conduits or channels. The control coil 22 can be configured to individually and independently or concurrently inflate the cells 14. The control coil 22 can have one or more wires to control steering of the device.

FIG. 3b illustrates that each cell 14 can have a single bellow 18.

FIG. 3c illustrates that the control coil 22 can have a first fluid port 42a in a first cell 14 and a second fluid port 42b in a second cell 14. The first and second fluid ports 42a and 42b can be in fluid communication with first and second fluid channels 38a and 38b within the control coil 22. Fluid pressure in the first and second fluid channels 38a and 38b can be individually controlled by a base unit 46.

Figure 4:
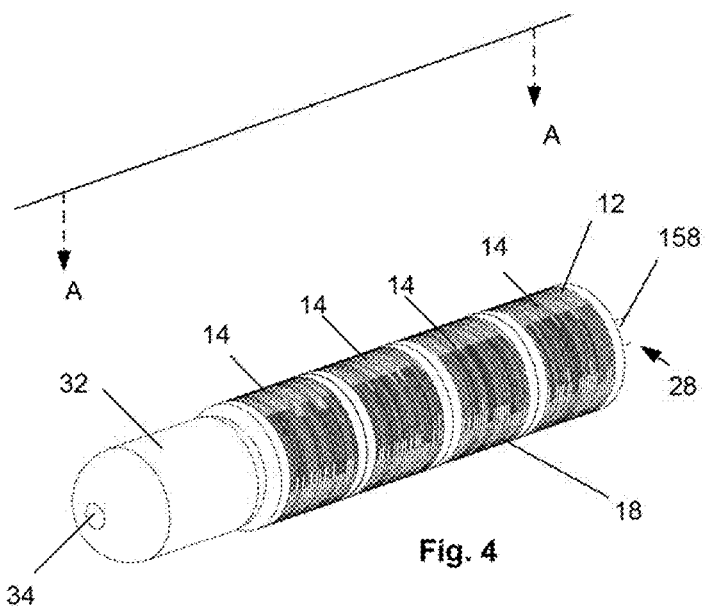
FIG. 4 illustrates a variation of the biological navigation device in a longitudinally contracted configuration.
Figure 5:
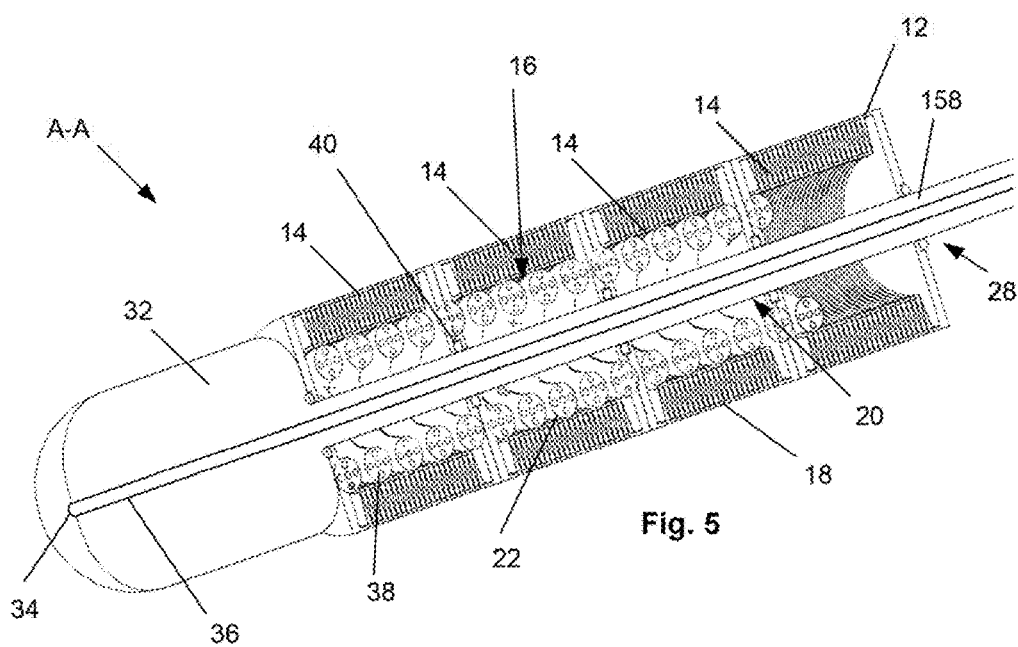
FIG. 5 illustrates a variation of cross-section A-A of FIG. 4.

FIGS. 4 and 5 illustrate that the elongated element 28 can be received inside the tool channel 20. The elongated element 28 can have a distal component 32 at the distal end of the elongated element 28. The elongated element 28 can have a umbilical 158 extending proximally from the distal component 32. The elongated element 28 can have a working channel and/or controls (e.g., data and/or power wires) for lighting (e.g., LEDs), visualization (e.g., CMOS), tools, or combinations thereof. The cells 14 can have cell seals 40 (e.g., o-rings) between each adjacent cell 14 and/or at the ends of the cells 14 and/or between the cells 14 and the tool channel 20 and/or elongated element 28.

The control coil 22 can be contained within the cells 14. The control coil 22 can pass from a first cell 14 to a second cell 14.

Figure 6B:
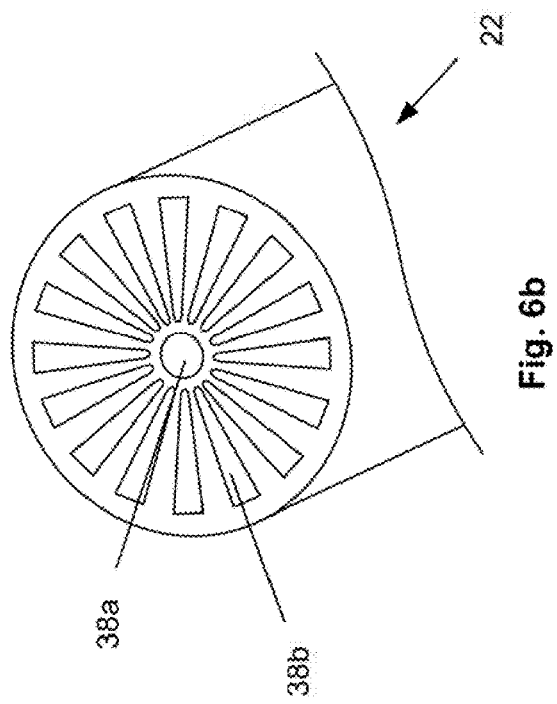
FIGS. 6a and 6b illustrate variations of a transverse cross-section of the fluid conduit.
Figure 6A:
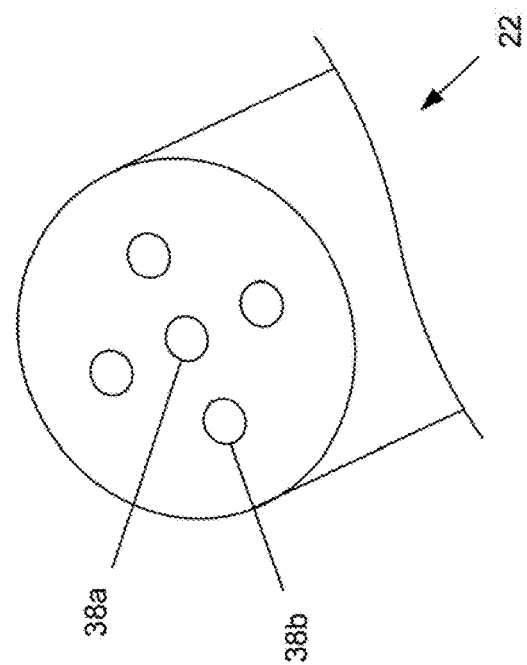

FIG. 6a illustrates that the control coil 22 can have numerous (e.g., about live) fluid channels 38 or conduits. The channels can have circular cross-sections. The channels can be arranged equi-angularly around the center of the control coil 22. Each fluid conduit can be configured to inflate a separate cell 14.

A first channel can extend along the center of the control coil 22. Any or all of the channels can be used to supply fluid pressure to the cells 14 and/or fluid, power, data, tissue samples or grafts, or combinations thereof to or from the distal component 32.

FIG. 6b illustrates that the fluid channels 38 can be transversely or radially elongated. For example, the cross-section of the fluid channels 38 can be substantially triangular, as shown. The control coil 22 can have, for example, about 16 fluid conduits.

Figure 7:
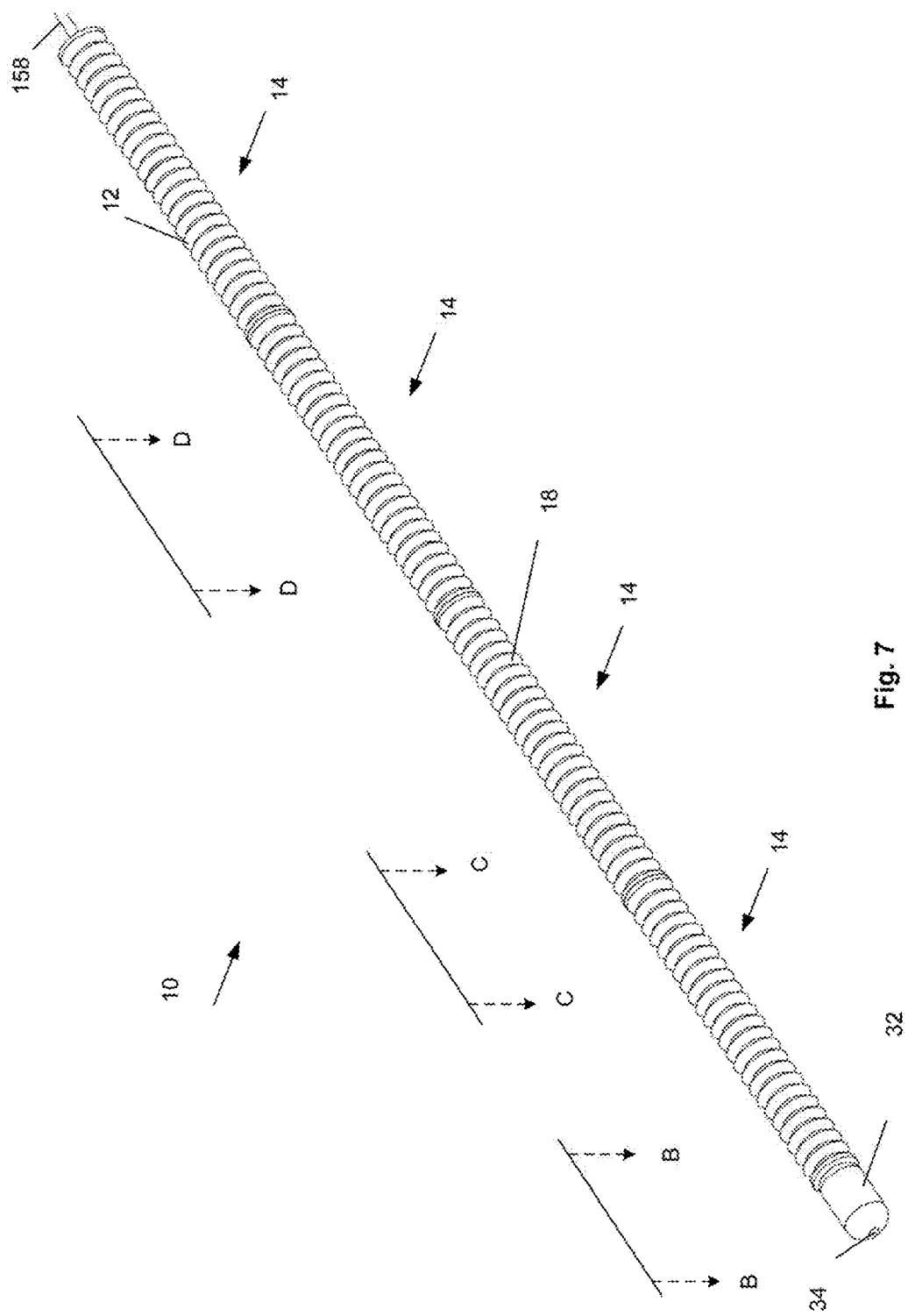
FIG. 7 illustrates the biological navigation device of FIG. 7 in a longitudinally expanded configuration.

FIG. 7 illustrates that the cells 14 can be inflated.

Figure 8A:
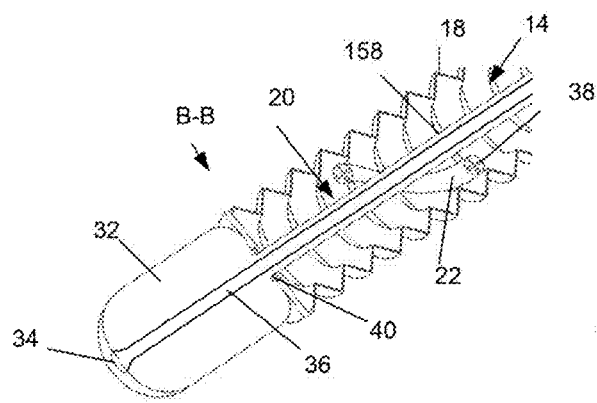
FIG. 8a illustrates a variation of cross-section B-B of FIG. 7.

FIG. 8a illustrates that in the longitudinally expanded configuration, the control coil 22 can longitudinally expand. The control coil 22 can provide structural radial support. Mechanical manipulation of the control coil 22, for example via one or more control leads or wires integral with or attached to the control coil 22, can steer the biological navigation device 10.

The working channel 36 can be equi-radial to the working channel port 34 and/or the working channel 36 can have a trumpeting configuration as the working channel 36 approaches the working channel port 34.

Figure 8B:
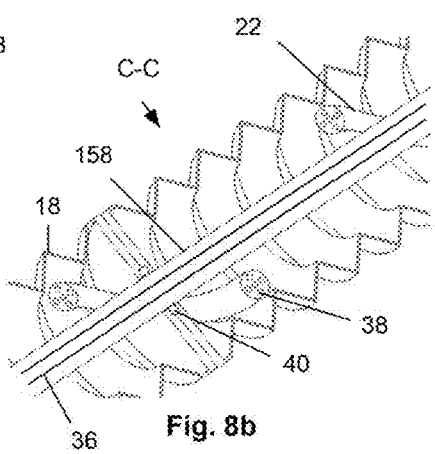
FIG. 8b illustrates a variation of cross-section C-C of FIG. 7.

FIG. 8b illustrates that the control coil 22 can pass between adjacent cells 14 without creating direct fluid communication between the bladders 16 of the adjacent cells 14. For example, the control coil 22 can be integrated (e.g., jointly molded) into the cell wall, or surrounded by a control coil 22 seal (not shown) to minimize or completely prevent fluid leakage between the adjacent cells 14.

Figure 8C:
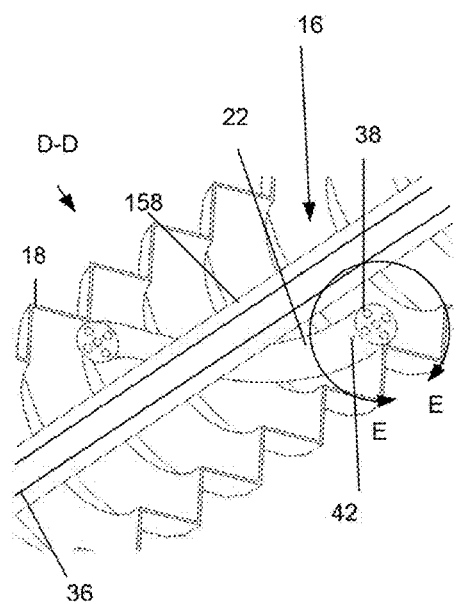
FIG. 8c illustrates a variation of cross-section D-D of FIG. 7.
Figure 8D:
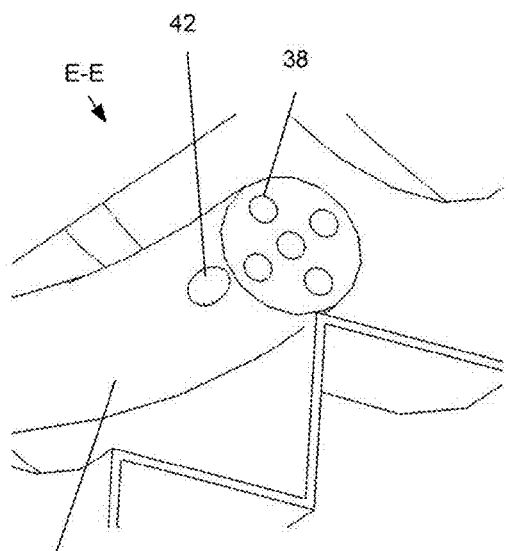
FIG. 8d illustrates a variation of cross-section E-E of FIG. 8c.

FIGS. 8c and 8d illustrate that the control coil 22 can have a fluid port 42 on the side of the control coil 22. One or more fluid ports 42 can be located on the control coil 22 within each cell 14. The fluid ports 42 located within a single cell 14 can be in fluid communication with the same fluid channel 38. For example, the fluid ports 42 in the first cell 14 can be in fluid communication with the first fluid channel 78a. The fluid ports 42 in the second cell 14 can be in fluid communication with the second fluid channel 78b.

FIGS. 9a and 9b illustrate that a traveler channel 49 can extend along the longitudinal axis, for example along the elongated element 28, for example the umbilical 158. The biological navigation device 10 can have a pressure traveler 44. The pressure traveler 44 can be slidably received by the cells 14. For example, the pressure traveler 44 can be threadably slidably received by the traveler channel 49 in the umbilical 158 which is slidably received in the tool channel 20 in the cells 14. The biological navigation device 10 can be configured so the pressure channel can controllably deliver and/or withdraw fluid pressure to one or more cells 14, for example causing the cells 14 to longitudinally expand and/or contract.

The distal end of the base 46 can have a trumpeted abutment, for example, to prevent the base 46 (except the proximal stiffener 152 when the proximal stiffener 152 is attached to the base 46) from entering the anus during use.

Figure 9C:
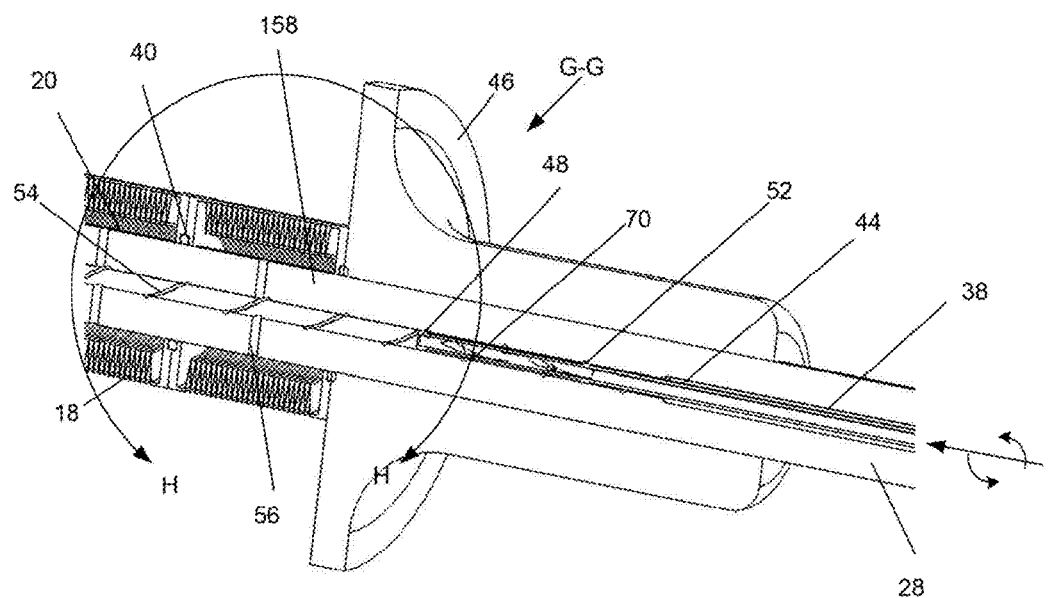
Figure 9D:
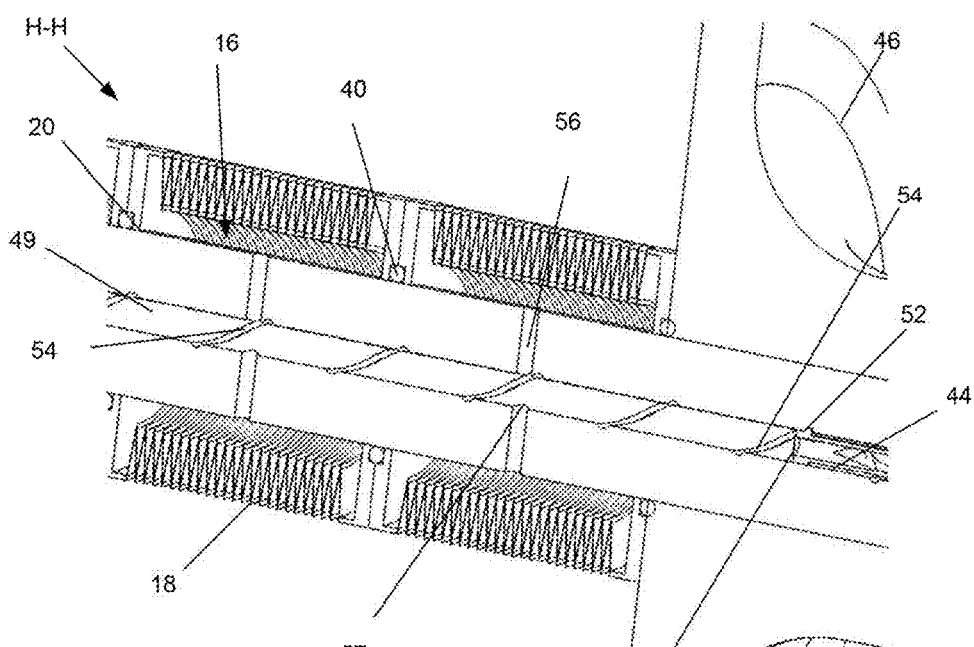
FIG. 9d illustrates a variation of close-up H-H of FIG. 9c.

FIGS. 9c and 9d illustrate that the pressure traveler 44 can have a fluid channel 38. The fluid channel 38 can be a hollow conduit in the pressure traveler 44. The fluid channel 38 can have a traveler cap 48 at the distal end of the fluid channel 38. The pressure traveler 44 can be translated and rotated (i.e., screwed), as shown by arrows, into and out of the traveler channel 49. The elongated element 28, for example in the umbilical 158, can have one, two or more umbilical pressure channels 57 between the traveler channel 49 and the bladder 16 of the cell 14. The traveler channel 49 can have a umbilical pressure port 57 opening into each umbilical pressure channel 56.

The traveler channel 49 can have a traveler groove 54, for example forming a helical configuration along the traveler channel 49. The pressure traveler 44 can have one or more traveler rails 52 (e.g., pegs, threads) configured to sealably and/or slidably engage the traveler groove 54.

FIGS. 10a and 10b illustrate that the proximal-most cell 14 of the biological navigation device 10 can be longitudinally expanded or extended, for example by inflating the cell 14. The pressure traveler 44 can be translated and rotated, as shown by arrows, further distal (or proximal) along the biological navigation device 10 after inflating the inflated cell 14. The pressure traveler 44 can be left in place after inflating the inflated cell 14.

Figure 10C:
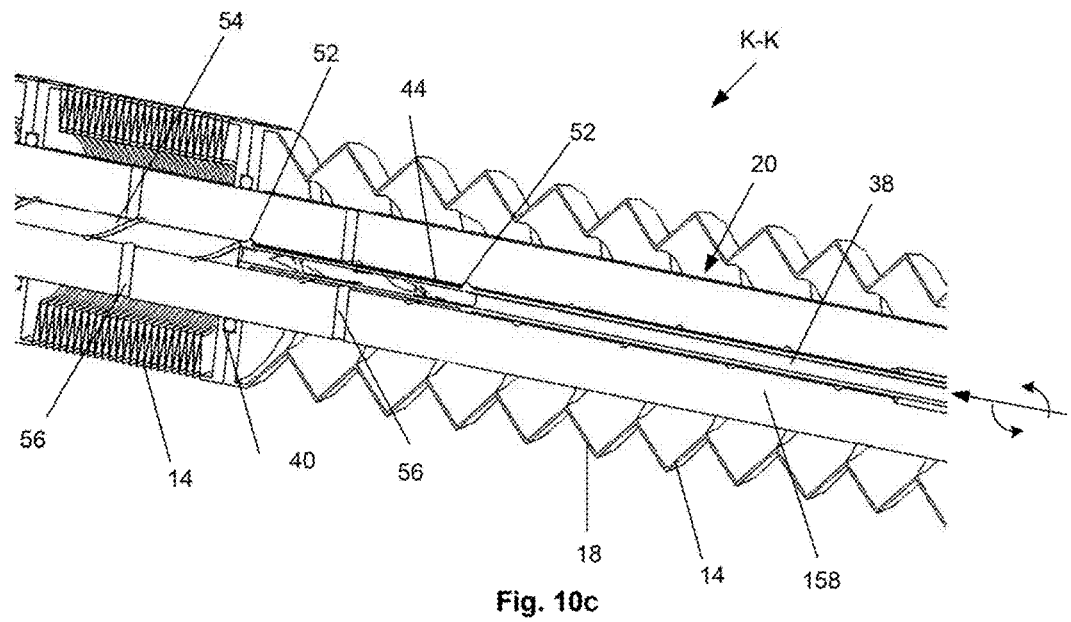
Figure 10D:
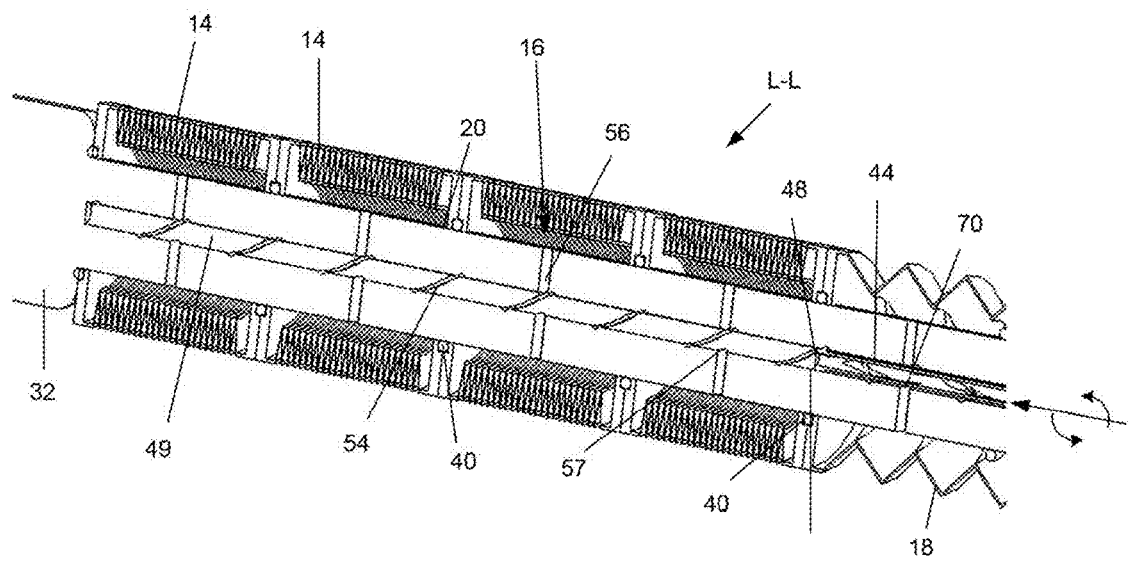
FIG. 10d illustrates a variation of close-up L-L of FIG. 10c.

FIGS. 10c and 10d illustrate that the pressure traveler 44 can controllably deliver fluid pressure to one or more selected umbilical pressure ports 57. The pressure traveler 44 can have a pressure exit port 42. The pressure exit port 42 can be on the side of the fluid channel 38. The pressure exit port 42 can be placed in an adjacent position to the umbilical pressure port 57. The fluid channel 38 can be pressurized by an external pump (e.g., attached to the proximal end of the pressure traveler 44). The fluid pressure in the pressure traveler 44 can be delivered through the pressure exit port 42 and the umbilical pressure port 57, and through the umbilical pressure channel 56 and into the bladder of the cell 14.

The bladder of the cell 14 can be substantially fluid-tight for each cell 14 when the pressure traveler 44 is not delivered or withdrawing fluid pressure. For example, the cell seal 40 can form a fluid-tight seal between the elongated element 28 and the cell wall. The umbilical pressure channel 56 and umbilical pressure port 57 can be sealed against the pressure traveler 44 when the pressure exit port 42 is not aligned with the umbilical pressure port 57.

FIGS. 11 through 24 depict articulatable sections 66 of the device. The articulatable section 66 can have multiple links 78 and one or more cables 80 passing through the links 78. The cables 80 can be used to control the articulation of the links 78. The links 78 have flanges 84 and flange seats which can enable rotation and side location of the biological navigation device 10.

Figure 11:
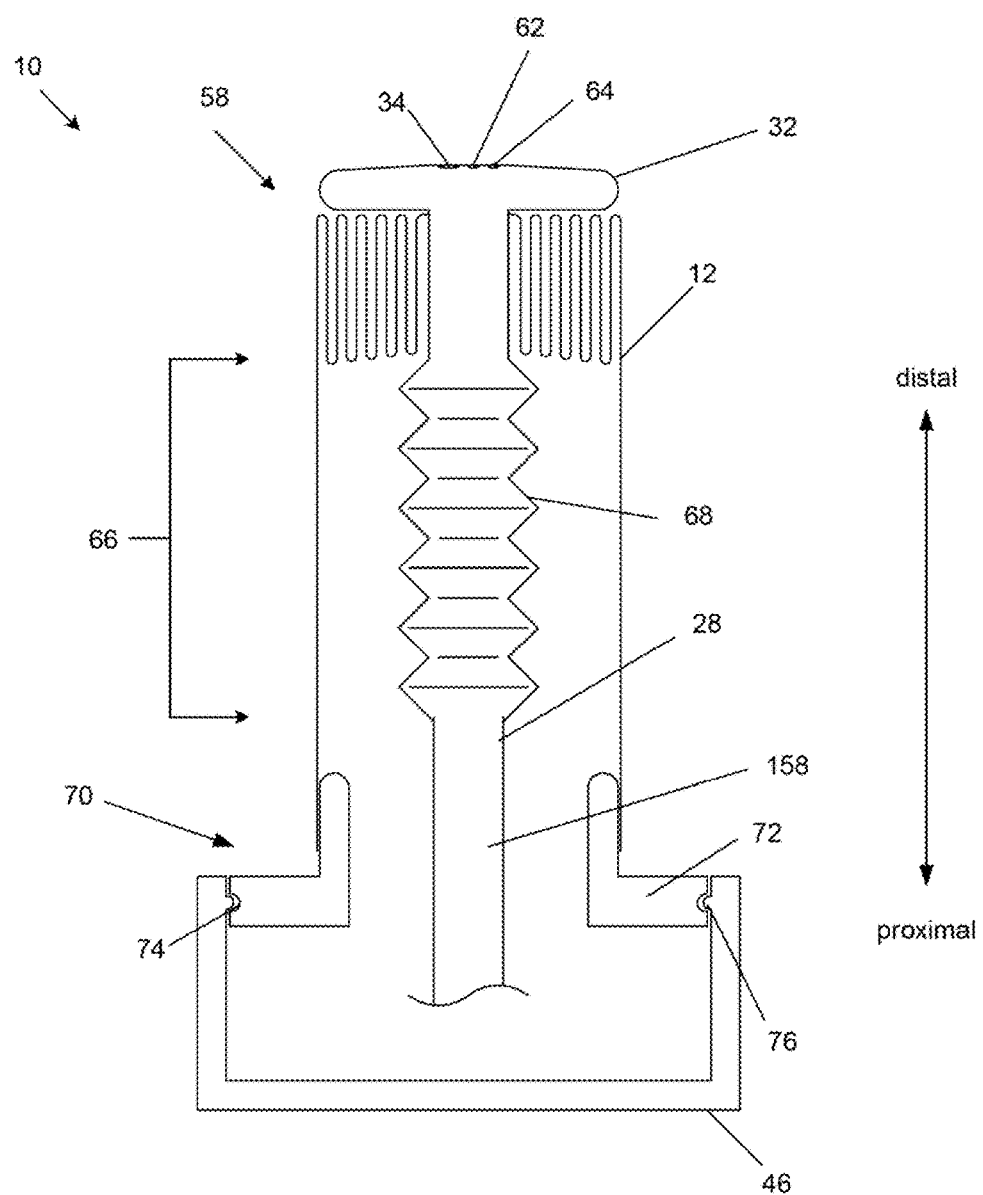
FIG. 11 illustrates a cross-section of a variation of the biological navigation device.

FIG. 11 illustrates that the device can have or be attached to (e.g., in the elongated element 28) a steerable section, for example articulating links 78 or an otherwise articulatable section 66. A distal end of the biological navigation device 10 can be distal to all or a substantial portion of the steerable section. Alternatively, the distal end of the biological navigation device 10 can be proximal to all or a substantial portion of the steerable section.

The articulatable links 78 can be individually and/or concurrently articulatable.

The tube 12 can be configured to be an everting tube. The tube 12 can have stowed tube material at a distal end 58 of the tube 12. For example, the stowed material can be scrunched, bunched, folded, otherwise compacted, or combinations thereof. The folds can be substantially parallel (as shown) or perpendicular to the longitudinal axis of the tube 12. The proximal end of the tube 12 can be attached to or integral with a tube connector 72.

The device can have a base 46. The base 46 can have an exit port 70. The tube connector 72 can be removably attachable to the base 46 at the exit port 70. For example, the tube connector 72 can have a tube connector interlock 74 that can removably attach to a base interlock 76 on the base 46. The interlocks can be a peg, rail, hole or other receiver, snap, thread, or combinations thereof. The tube 12 and tube connector 72 can form a cartridge. The cartridge can seal to a base unit with a fluid seal that is located in either the base unit or in the cartridge or cassette (e.g., along the tube connector 72, for example at the tube connector interlock 74 and/or base interlock 76). The cartridge can have a substantially disposable product life.

The base 46 can controllably deliver fluid pressure to the inside of the tube 12. For example, the base 46 can controllably deliver pressure independently to the different fluid channels 38 of the device. The base 46 can control the articulating links 78, for example via one or more control leads, wires, cables 80, or combinations thereof.

The distal component 32 of the elongated element 28 can have a camera or other visualization element 62. The distal component 32 can have one or more elements that enable vision (e.g., fiber optics, CCD cameras, CMOS camera chips) and/or lighting (e.g., fiber optic light sources, high power LEDs (Light Emitting Diodes)), such as lighting element 64. The distal component 32 can have the working channel port 34, for example to provide suction or pressurization, fluid irrigation, the delivery of instruments (e.g., for cutting, coagulation, polyp removal, tissue sampling) and lens cleaning elements (typically a right angle tool or orifice that can exit near the camera, such that a fluid flush provides a cleansing wash).

In an exemplary variation, the elements, in order from the proximal end of the device to the distal end of the device (including the elongated element 28), can include: the base 46, the tube 12, the steering mechanism, the distal end of the tube 12, and the distal component 32, for example, including lighting and vision and working channel exit.

FIG. 12 illustrates a variation of the articulatable section 66 of the device. The articulatable section 66 can have multiple links 78 and one or more cables 80 passing through the links 78. The cables 80 can be used to control the articulation of the links 78. As tensile cables pull from the periphery of the articulating sections, the cables 80 can impart torques, which rotate the links 78 on the axes of rotation of the links 78, articulating the articulatable section 66.

The links 78 can be rotatable attached to adjacent links 78. For example, a first link 78a can be attached at a first end to a second link 78b. The first link 78a can rotate with respect to the second link 78b only about a first axis. The first link 78a can be attached at a second end to a third link. The first link 78a can rotate with respect to the third link only about a second axis. The first axis can be non-parallel to the second axis. For example the first axis can be perpendicular to the second axis. The first and second axes can be non-parallel to a longitudinal axis of the articulatable section 66. For example, the first and second links 78a and 78b can be perpendicular to the longitudinal axis of the articulatable section 66.

FIG. 13 illustrates that the link can have one, two or more first flanges 84a pointed in a first longitudinal direction. The link can have one, two or more second flanges 84b pointed in a second longitudinal direction. The first flanges 84a can each have a first pivot hole 88. The second flanges 84b can each have a second pivot hole 90. With adjacent links 78 in an assembled configuration (as shown in FIG. 13), a pivot pin (not shown) can be inserted through the pivot holes. The hinges being integral with the links 78 can eliminate the need for separate hinge pins to rotate about.

The link can have flange seats 86. The flange seats 86 can be configured to receive the flanges 84 from the adjacent links 78.

The link can have one, two, three, four or more cable through-holes 92. The cable through holes 92 can be aligned in a longitudinal direction. The cable through holes 92 can be configured to slidably receive a control cable, wire, lead, or combination thereof. Cable through holes 92 that are off-axis from pin locations can allow for smaller diametrical profiles while still maintaining large pin surfaces of rotation. This arrangement can enable pulling dual cables 80 to actuate about a pin axis, with superior additive forces resulting.

The link can have a centered link longitudinal axis. The angle with respect to the link vertical axis 82 between a cable through-hole and the adjacent pivot hole can be an adjacent cable-to-pivot hole angle 94. The adjacent cable-to-pivot hole angle 94 can be from about 10° to about 90°, for example about 45°.

FIG. 14 illustrates an articulatable section 66 constructed from the links 78 shown in FIG. 13. The articulatable section 66 can be configured in maximum flexion, as shown. The articulatable section 66 can have a radius of curvature 104 from about 2.5 mm (0.1 in.) to about 25 mm (1.0 in.), for example about 15 mm (0.6 in.).

Figure 15:
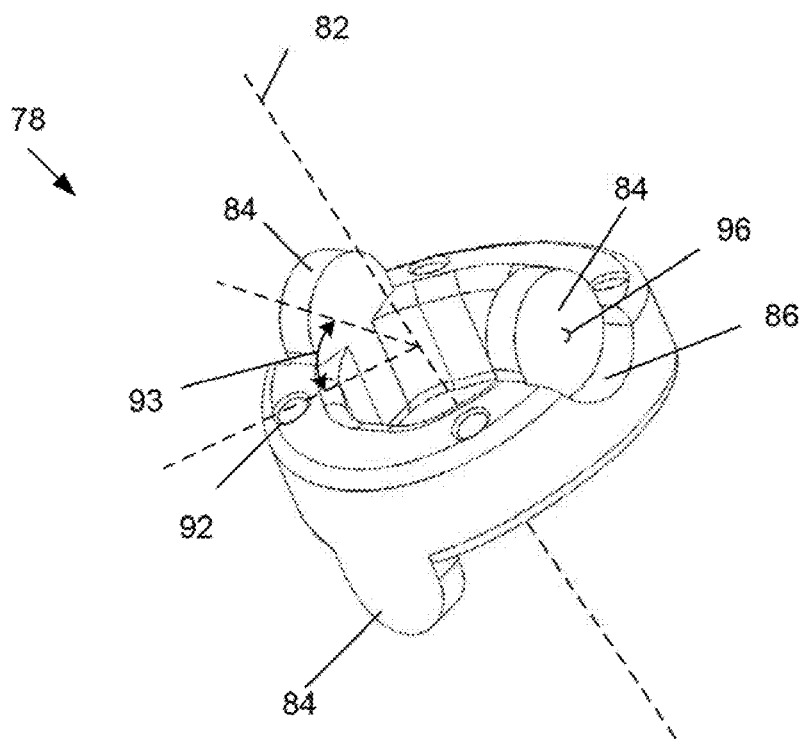
FIG. 15 illustrates a variation of the link.
Figure 16:
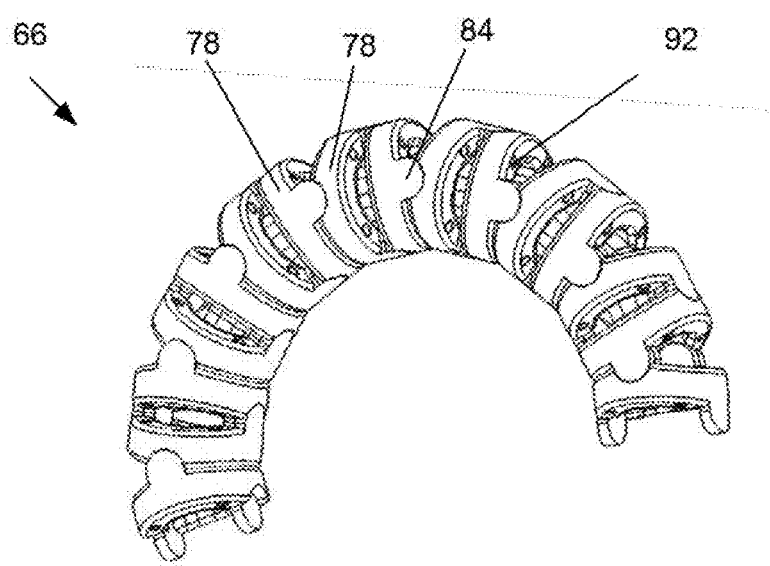
FIG. 16 illustrates a variation of the articulatable section having the links of FIG. 15.

FIGS. 15 and 16 illustrate links 78 that can be attached to adjacent links 78 without pivot or other pins. The flange on a first link 78a can be configured to press against the adjacent flange on an adjacent second link 78b to rotatably attach the first flange 84a to the second flange 84b. The links 78 can be longitudinally compressed to remain attached to the adjacent links 78. For example, the compression can be due to tension in the cables 80 in the cable through-holes 92.

Each flange can have a nipple 96 and/or nipple seat (not shown) located on the axis of rotation of the flange. The nipple 96 and/or nipple seat can rotatably attach to the adjacent nipple 96 or nipple seat on the adjacent flange. The nipple 96 can rotatably interlock into the nipple seat.

The link can have an adjacent cable hole-to-flange angle 93. The adjacent cable hole-to-flange angle 93 can be from about 10° to about 90°, for example about 45°.

The cables 80 in the cable through-holes 92a and 92b can be pulled in combination or alone to induce a controlled articulation of the articulatable section 66. The multiple cables 80 can be used to concurrently impart the multiple (shown as two) cables' force on one side of the rotational axis of the first (or second) flange.

FIG. 16 illustrates an articulatable section 66 constructed from the links 78 shown in FIG. 15. The articulatable section 66 can be free of pins needed for rotation of the links 78.

Figure 17A:
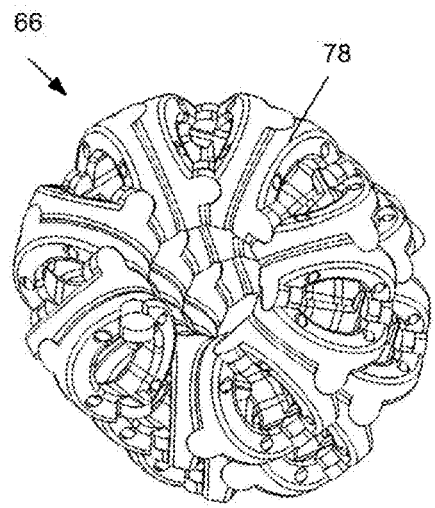
FIGS. 17a and 17b are end and side views, respectively, of a variation of the articulatable section having the links of FIG. 13 in a maximum articulation configuration.
Figure 17B:
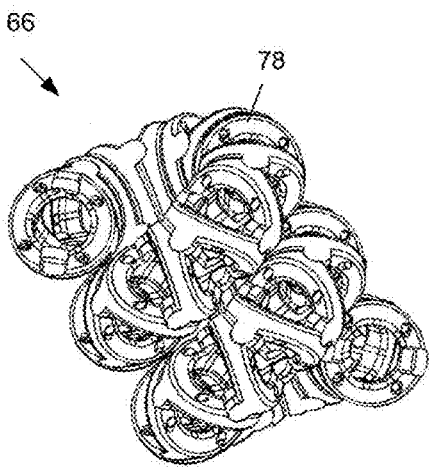

FIGS. 17a and 17b illustrate that the articulatable section 66 can form a tight coil without interfering with other turns of the coil. The links 78 can have offset configurations that allow them to coil back without hitting themselves. This allows the links 78 to, among other things, create a more dynamic range of tip-controlled views that are possible for the tip-located vision system, for example for use with polyp detection.

Figure 18:
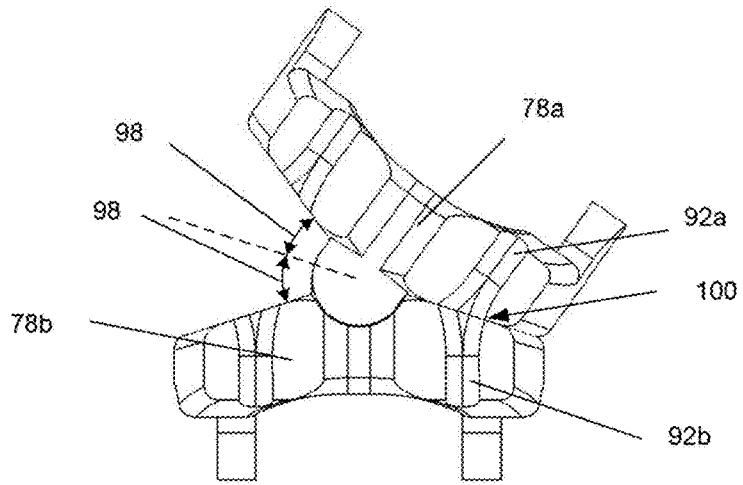
FIG. 18 is a partial cut-away view of a variation of adjacent links.

FIG. 18 illustrates that the when adjacent links 78 are in full flexion with respect to each other, the links 78 can have a maximum link angulation 98.

The first link 78a can have a first cable through-hole 92a. The second link 78b can have a second cable through-hole 92b. When the first and second links 78a and 78b are at maximum flexion, the point where first cable through-hole 92a meets the second cable through-hole 92b can be a cable crimp point 98. The cable 80 in the cable through-holes 92 can be crimped at the cable crimp point 98, for example because of the excessive tension and/or compression on the cable 80 from the cable making a sharp (e.g., acute) angled turn.

Figure 19A:
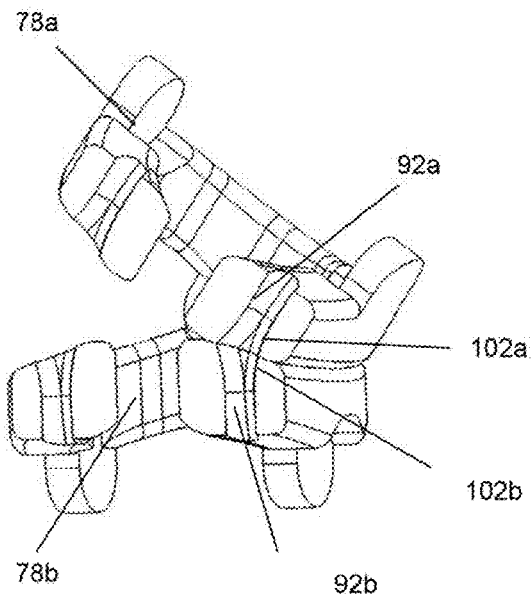
FIGS. 19a and 19b are partial cut-away views of a variation of adjacent links.
Figure 19B:
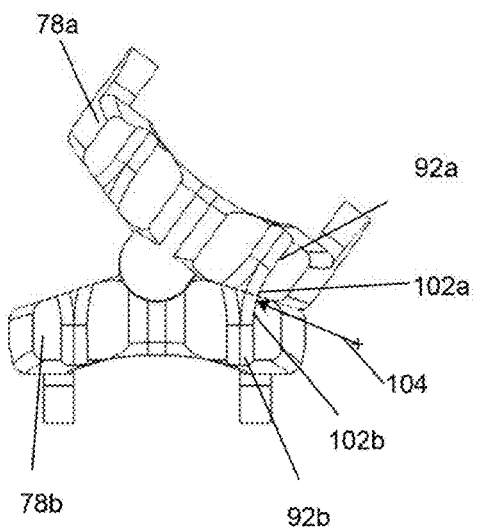

FIGS. 19a and 19b illustrate that the first cable through-hole 92a and/or the second cable through-hole 92b can have first and second circumferential chamfers 102a and 102b, respectively. The circumferential chamfers 102a and/or 102b can be radial widening of the cable through-holes, for example at one or both ends of the cable through-holes 92. When the first and second links 78a and 78b are in maximum flexion, the first and second cable through-holes 92a and 92b can have a continuous radius of curvature 104 between the first and second cable through-holes 92a and 92b (e.g., a smooth, rounded path). The continuous radius of curvature 104 can exist, for example, in the plane of motion for the given adjacent links 78.

Figure 20:
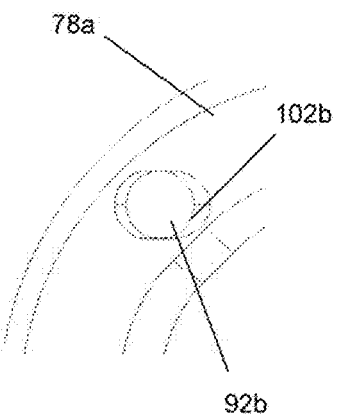
FIG. 20 is an end view of a cable through-hole from the links of FIGS. 12a and 12b.

FIG. 20 illustrates an end view of the second cable through-hole 92b showing the (second) circumferential chamfer 102b can be larger than remainder of the (second) cable through-hole 92b.

Figure 21:
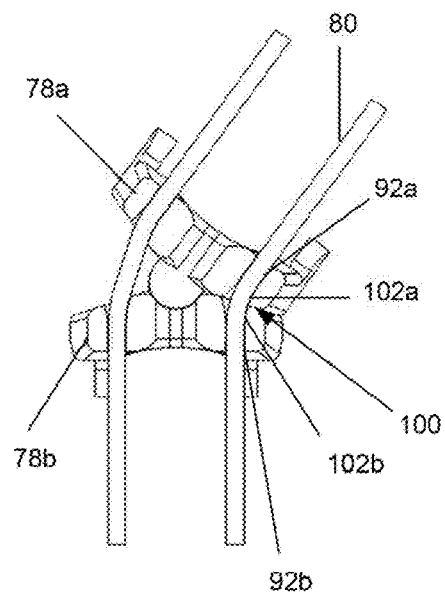
FIG. 21 illustrate partial cut-away views of a variation of the links of FIGS. 14a and 14b with cables.

FIG. 21 illustrates the cables 80 passing through the cable through-holes 92a and 92b with the smooth, rounded cable crimp point 98 with adjacent circumferential chamfers 102a and 102b. The circumferential chamfers 102a and 102b can reduce cable wear, link wear and friction.

Figure 22A:
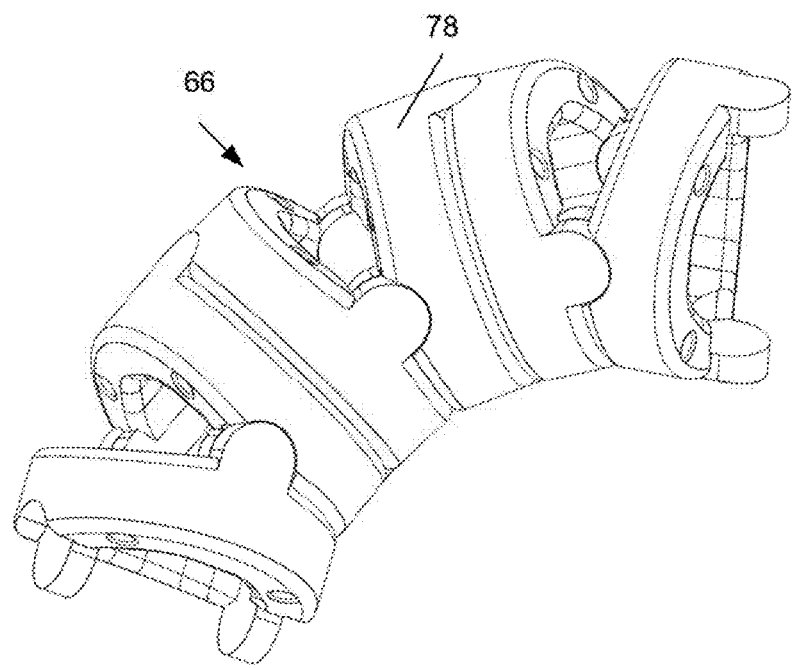
FIGS. 22a and 22b illustrate variations of the articulatable sections with varying link angulations.
Figure 22B:
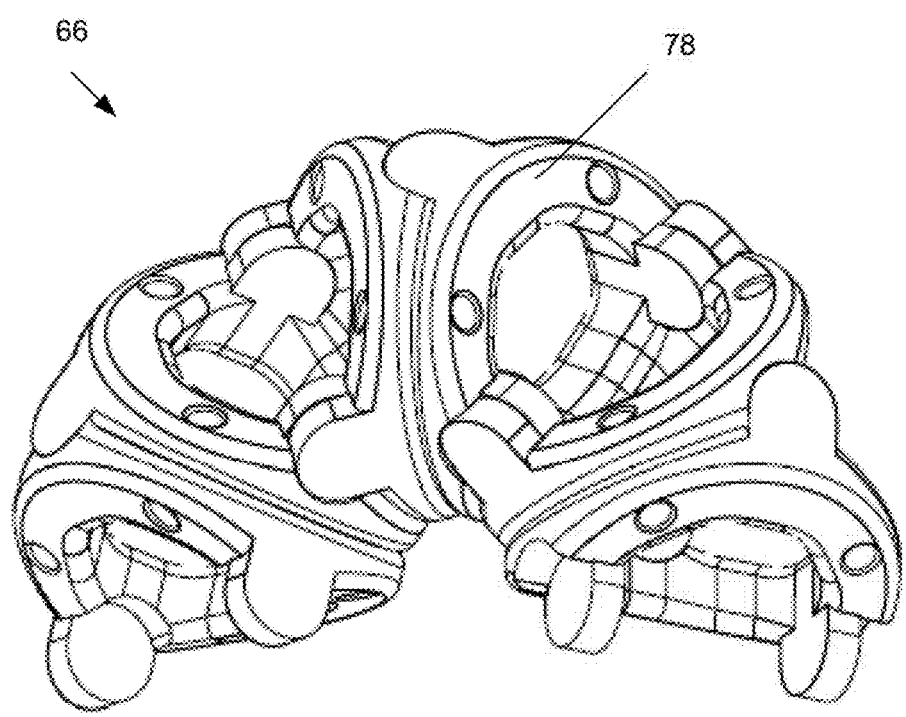

FIGS. 22a and 22b illustrate that link configuration can be modulated to achieve varying systems of curvature. The maximum link angulation 98 can be from about 5° to about 45°. For examples, FIG. 22a illustrates the maximum link angulation 98 of about 12°. FIG. 22b illustrates the maximum link angulation 98 of about 24°. The maximum link angulation 98 can also be, for example, about 15°, about 18°, or about 21°. Link angles can be consistent within an articulatable section 66, or they can modulate from link-to-link within an articulatable section 66. The thickness of the base of the link 78 can be increased to decrease the maximum link angulation 98. The thickness of the base of the link 78 can be decreased to increase the maximum link angulation 98.

The distal end of the device can be distal to all or a substantial portion of the steering section (e.g., the articulating links/section). The distal end of the device can be proximal to all or a substantial portion of the steering section (e.g., the articulating links/section). The steering section can be in or on the elongated element 28, the navigation device, a combination thereof. The various locations of the steering section can, for example, alter steering kinematics of the device.

Figure 23:
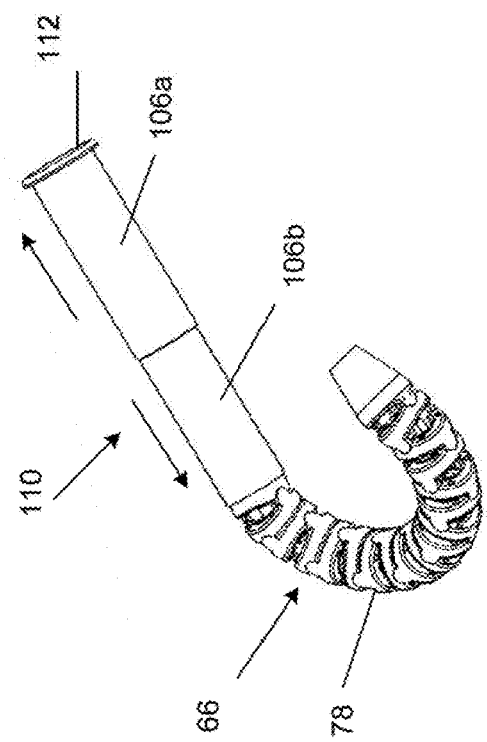
FIG. 23 illustrates a wireframe view of a variation of a reciprocatable section and an articulatable section with the reciprocatable section in an expanded configuration.

FIG. 23 illustrates that the device can have a reciprocatable section 110, for example a reciprocating distal end of the device. The reciprocating section can be translated back and forth with respect to the remainder of the device. The device can have a reciprocating actuator to reciprocate the reciprocating section. The reciprocating actuator can have one or more a pneumatic actuators (e.g., a dedicated element or as a function of an inflatable drive sleeve), cables 80, motors, higher pressure hydraulics, nitinol elements, smart muscle (e.g., electro active polymers), or combinations thereof. This reciprocating feature can enable the tip and its associated elements to move back and forth without the remainder of the biological navigation device 10 and/or the elongated element 28 moving. This can enable local close-up inspections and visualization without the need for motion of the entire biological navigation device. This can enable the ability to look in a certain direction and to go towards that point, without the movement of the entire device. This can enable the ability to assist in reduction and maneuverability, as it enables the ready ability to extend the tip to then manipulate tissue or move through tissue, when perhaps such a movement would be cumbersome for the wholesale system. This can be through a single reciprocating element, or through multiple elements, such as telescoping tube sections or bellows 18.

Figure 24:
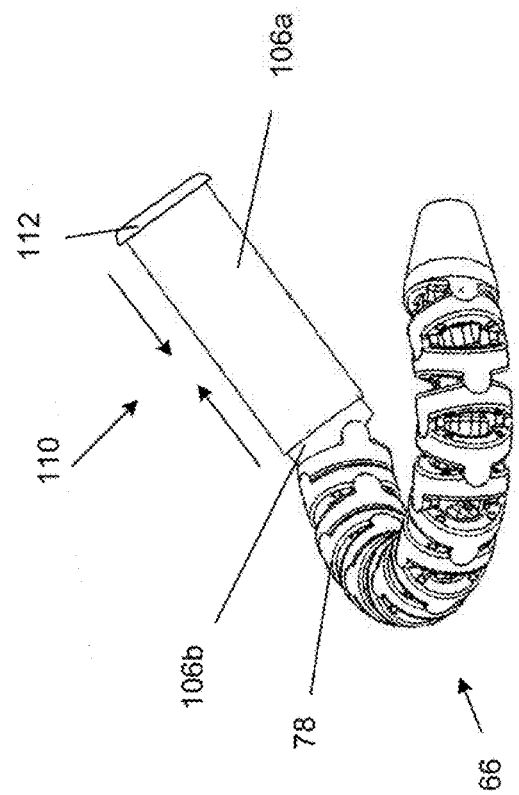
FIG. 24 illustrates a variation of a reciprocatable section and an articulatable section with the reciprocatable section in a contracted configuration.

The reciprocatable section 110 can have a first reciprocating element 106a that can translate with respect to a second reciprocating element 106b. The first reciprocating element 106a can have a distal tip 112 at the distal end of the first reciprocating element 106a. As shown by arrows in FIG 23, the first and second reciprocating elements 106a and 106b can translate away from each other. As shown by arrows in FIG. 24, the first and second reciprocating elements 106a and 106b can translate toward each other. As shown in FIGS. 23 and 24, the reciprocatable section 110 can be distal to the articulatable section 66. The reciprocatable section 110 can be proximal to the articulatable section 66.

The reciprocatable section 110 can be steered in any direction. The remainder of the device can then be advanced in that direction through the forward motion portion of the reciprocating element (e.g., the first reciprocating element and the second reciprocating element can be actuated to translate away from each other). Once the device has advanced, for example about 1" per reciprocation, the reciprocatable section 110 can have utilized the full value of the extensibility of the reciprocatable section 110. The tip can then stay where it is as the umbilical 158 is released at a rate equivalent to the tip reciprocating rate. Given that these rates are equivalent, they can when coupled to a system that is of high local buckling strength and environment engaged result in a tip distal point that is stationary, 'reset', and ready for the next advance.

The device can be configured to move with automation algorithms, for example through motor controls with the motors being either in the base 46 (e.g., connected to cables 80 in the tip) or with motors locally in the distal end of the device. Advancement of the device can be algorithm controlled. For example, if a section of the target biological lumen is substantially straight, the device can be translated without inchworming, so the forward advancement of the device can be controlled exclusively by other translational techniques. (e.g., releasing the umbilical 158 and/or translating the base 46 and/or tube 12 forward). As the distal tip 112 enters a torturous region, the device can begin inchworming motions. The inchworming motion can be used, for example, around corners of the target biological lumen. The distal tip extension can be highly controllable, steerable and reliable, and the equal and opposite motions can be difficult to control during unautomated (e.g., purely manual) use. Further the device can advance without the need for the typical anchors: radially expanding members, potentially damaging shear point, or suction.

The device can rely on internally produced reciprocating motion. The device can use its own mass that is simply lying against the colon surface as a reaction to assist the forward advancement of the device.

Electrical wires to the distal component 32 and the distal tip 112 can be configured to minimize bending of the wires. For example, the wires can have service loops of flexible wire members (e.g., including flex circuits). The working channels 36 and fluid conduits 38 can maintain their continuity and can be leak-free. The working channels 36 and fluid conduits 38 can have compressible members (e.g., bellows 18), and/or sliding members (e.g., telescoping sealed tubes).

The tension between the links 78 in the articulatable section 66 can be variably controlled. For example, the tension applied by the cable between the links 78 can be completely or substantially minimized to cause the links 78 to go limp. Causing the links. 78 to go limp can make the links 78 more readily pulled through the tube 12.

Figure 25A:
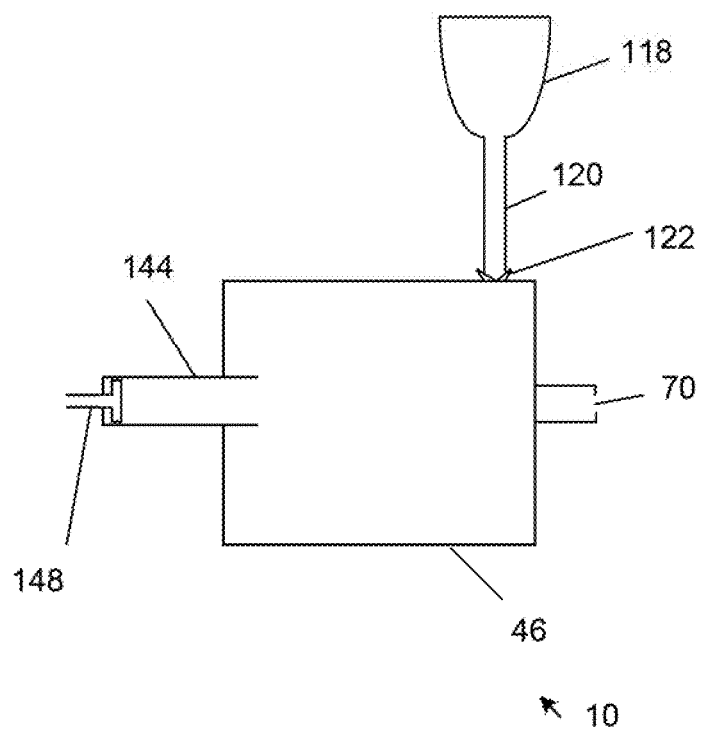
FIG. 25a illustrates a variation of a method for using the base.

FIG. 25*a* illustrates that a pump 144 having an extensible displacement component 148, such as a piston, can be used to pressurize the base 46. The piston or otherwise extensible displacement component 148 can be manipulated to control load volume to exert a corresponding pressure out of the exit port 70 and into the pressurizable tube 12 of the navigation device. The piston can minimize stored system energy. A fluid supply 118 can be attached to the base pressure port 122, for example via connecting tubing 120. The inlet port can have a one-way (i.e., check) valve preventing backflow. The exit port 70 can have a one-way (i.e., check) valve preventing backflow. The fluid supply 118 can be filled with fluid. The fluid can be delivered to the deployment system under no pressure or positive pressure. The fluid can be air, saline, water, carbon dioxide, nitrogen, or combinations thereof. The pump 144 can be separate from or attached to the base pressure port 122. For example, the fluid supply 118 can be routed through the pump 144 before or after passing through the base pressure port 122 and into the base.

Figure 25B:
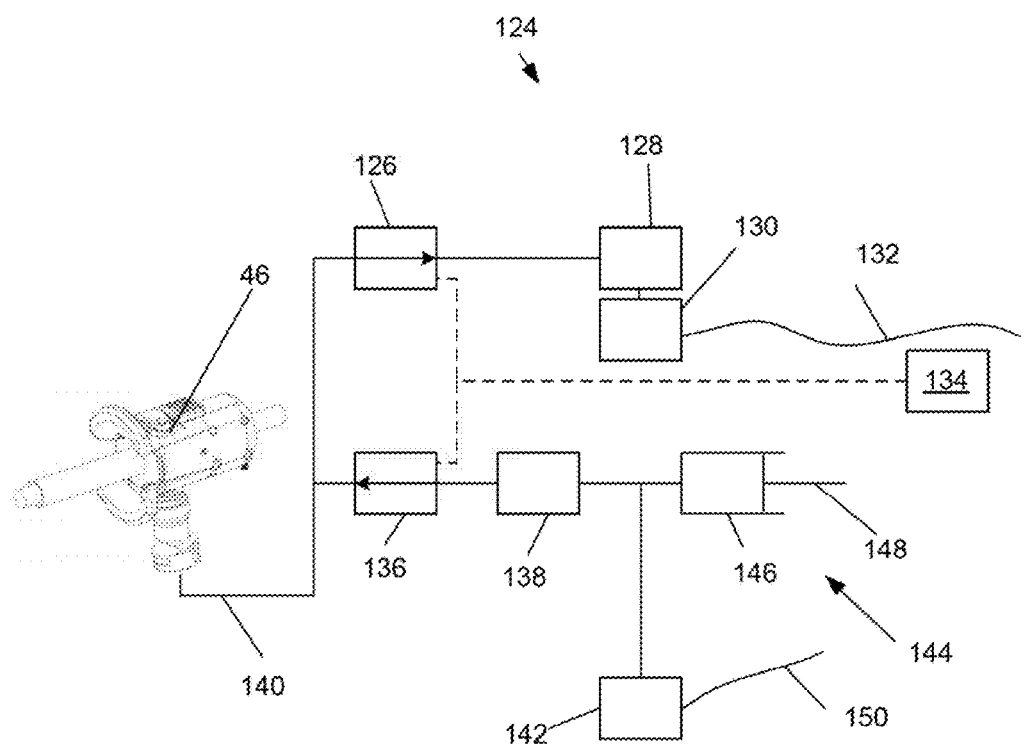
FIG. 25b is a schematic view of a variation of the base and a fluid system.

FIG. 25*b* illustrates that the base can be in fluid communication with a fluid control system 124. The base, for example at the base pressure port 122, can be connected to a pressure delivery line 140. The pressure delivery line 140 can be connected to an outgoing second valve 136 and/or an incoming first valve 126.

The first valve 126 can be configured to open manually and/or automatically. The first valve 126 can open when the tube pressure exceeds a maximum desired tube pressure. The first valve 126 can be connected to a vacuum pump 128. The vacuum pump 128 can be activated to deflate the tube 12 and withdraw the tube 12 or reduce the tube pressure. The vacuum pump 128 can be attached to an exhaust tank and/or directly to a bleed or drain line 132. The exhaust tank 130 can be connected to the drain line 132, for example to exhaust overflow from the exhaust tank 130.

Controls 134 can be in data communication with the first valve 126 and the second valve 136. The controls 134 can be on the base (e.g., a button or switch on the base).

The second valve 136 can be attached to a pump 144, for example a cylinder 146 with a displacement component 148, such as a piston. A pressure regulator 138 can be in the flow path between the pump 144 and the second valve 136. The pressure regulator 138 and/or the first valve 126 can open and release pressure from the pump 144 when the tube pressure exceeds a maximum desired tube pressure.

An intake tank 142 can be fed in line (as shown) or through the pump 144 to the second valve 136, for example through the pressure regulator 138. The fluid in the intake tank 142 can be fed into the pressurized tube 12. The intake tank 142 can have a fill line 150 for filling the intake tank 142 with fluid. The fill line 150 can be fed directly to the second valve 136, pressure regulator 138 or pump 144 without the intake tank 142.

The biological navigation device 10 can have capital equipment which can provide utility to the remainder of the device. The capital equipment can include, for example, the elements in the fluid control system 124. The fluid control system 124 can have a fluid source (e.g., the intake tank 142 and/or fill line 150), a pressusre source such as the pump 144, a conduit for delivery of the pressurization media (e.g., the pressure delivery line 140), controls 134, system monitoring elements (e.g., can be in the controls 134). The capital equipment can reduce the profile of the tube 12, for example, in which tools can be inserted. The integrated tools can create elements that reduce waste, thereby allowing for higher value capture and less refuse.

The fluid pressurization can be controlled by a variety of user inputs, for example a button on the elongated element 28 or base, voice commands, foot pedals, or combinations thereof.

FIG. 26 illustrates that the base can be handheld. The base can have a proximal stiffener 152 or introducer. The proximal stiffener 152 of the base can be inserted into the anus 154. The base pressure port 122 can be connected to a pressure source, such as the pump 144 and/or a fluid supply 118, before or after inserting the proximal stiffener 152. The base can be attached to the tube 12 (not shown, as the tube 12 is in the patient).

The anus 154 can provide entry into the colon 156 for a colonoscopy. The colon 156 extends from the rectum 160 to the cecum and has sigmoid, descending, transverse and ascending portions. The sigmoid colon 162 is the s-shaped portion of the colon 156 between the descending colon 164 and the rectum 160.

A colonoscopy can include inserting the proximal stiffener 152 and/or elongated element 28 into the anus 154. To navigate the colon 156, the forward few inches of the proximal stiffener 152 or the elongated element 28 can be flexed or steered and alternately pushed, pulled, and twisted. Once inserted, the biological navigation device 10 can navigate to the end of the colon 156: the cecum 170.

Figure 27B:
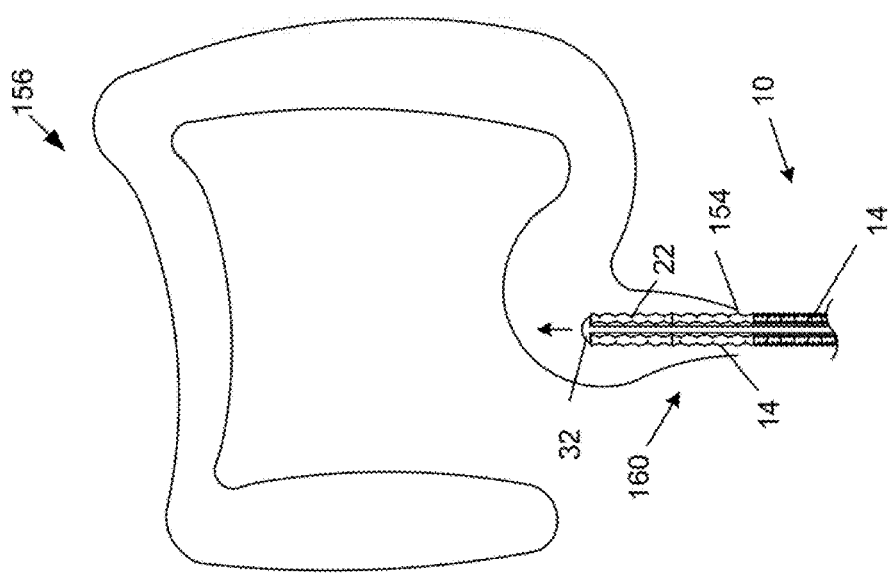
Figure 27A:
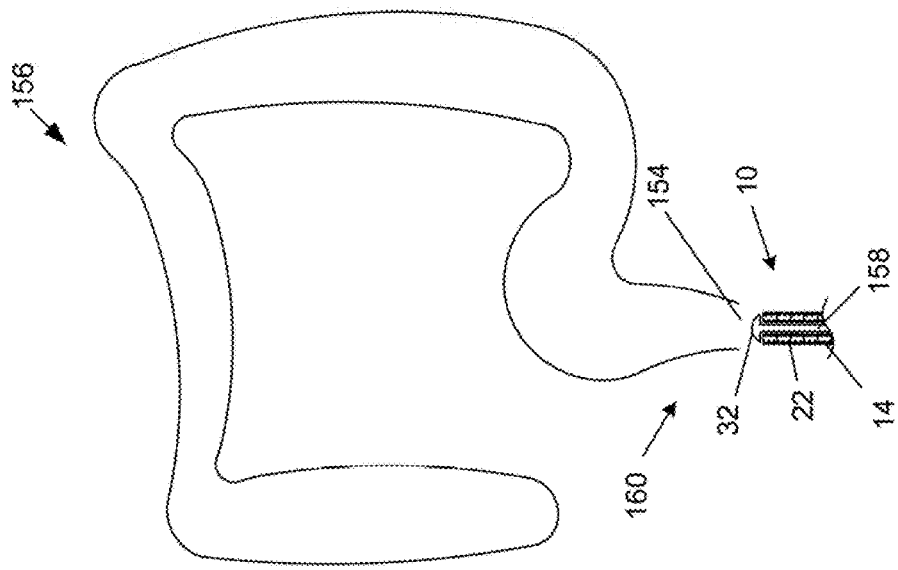

FIG. 27a illustrates that the biological navigation device 10 can be positioned before entry into the colon 156, for example via the rectum 160 after passing the anus 154. FIG. 25b illustrates that the pressure in the distal-most cell or cells 14 can be increased and/or the biological navigation device 10 can be otherwise deployed. The biological navigation device 10 can translate, as shown by arrow, into the rectum 160, attached to the elongated element 28.

The biological navigation device 10 is shown having an outer diameter smaller than the inner diameter of the colon 156 for exemplary purposes. The biological navigation device 10 can have an outer diameter about equal to the inner diameter of the colon 156. For example, the tube 12 can flexibly expand to substantially fill the cross-section of the length of the colon 156 occupied by the biological navigation device 10.

Figure 27D:
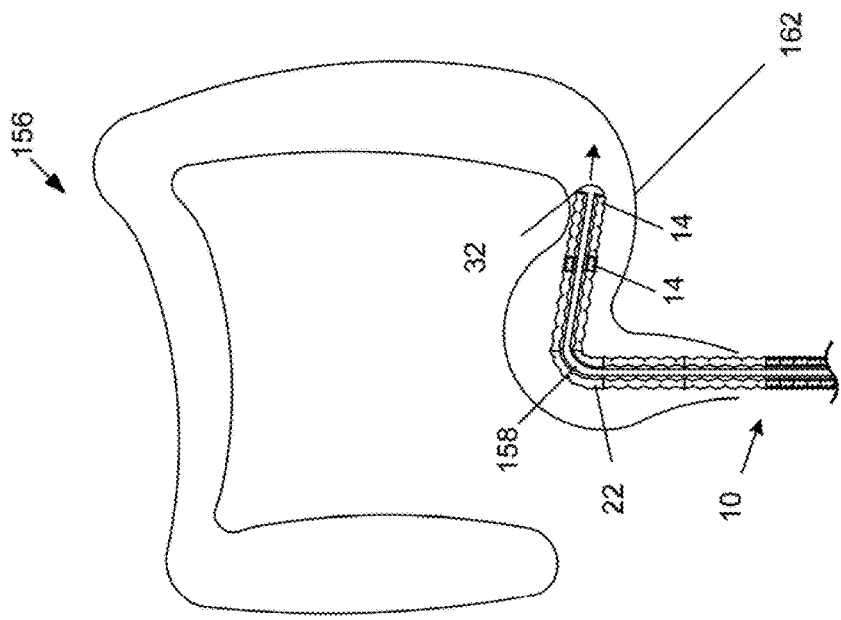
Figure 27C:
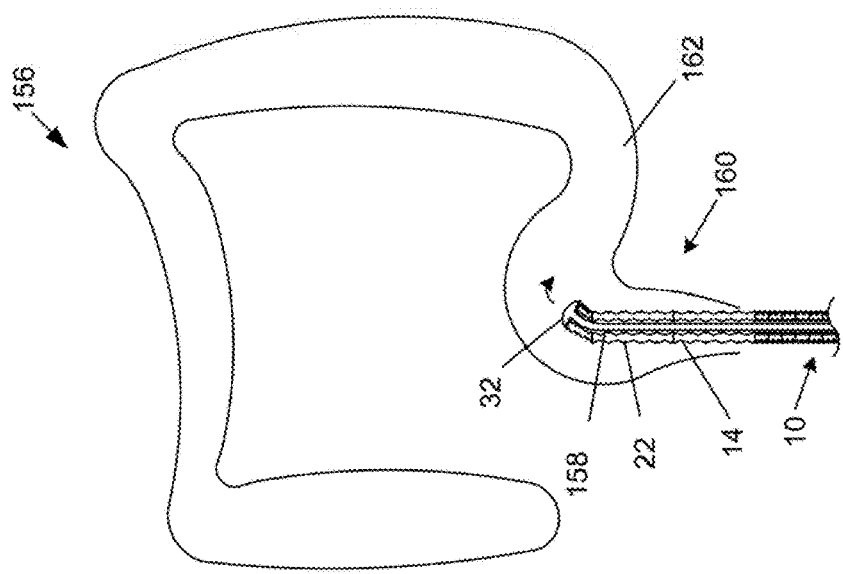
Figure 27F:
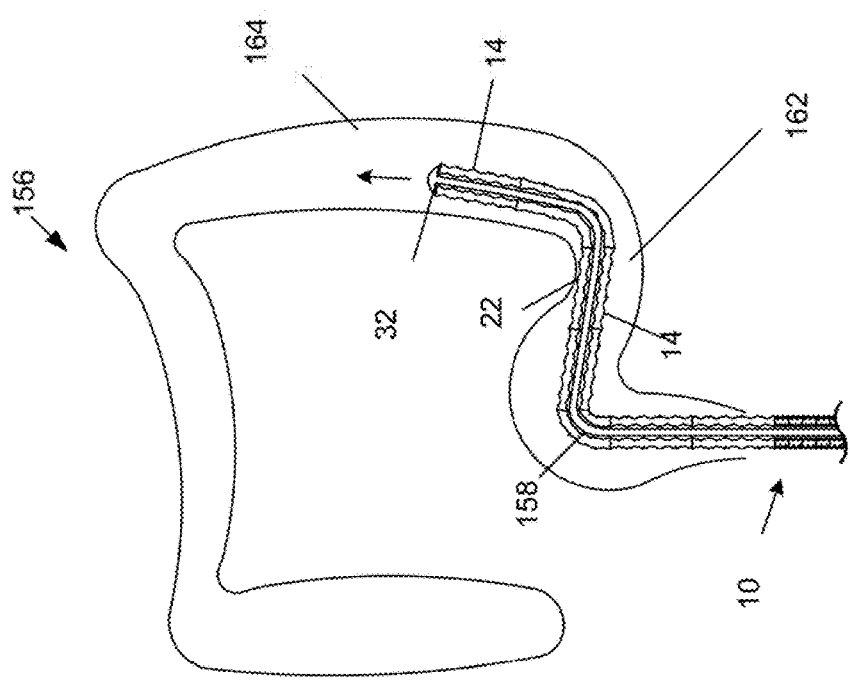

FIG. 27c illustrates that the distal end of the biological navigation device 10 can actively or passively flex in a 'cone of motion', with one portion of that plane of motion depicted by the arrow. The distal end of the biological navigation device 10 can actively rotate, for example by actuation of one or more control wires and/or actuators in or attached to the distal component 32 or head, such as the articulating section and/or control coil 22 described supra.

The distal end of the biological navigation device 10 can passively rotate, for example if the biological navigation device 10 (e.g., the tube 12 and/or the distal component 32) contacts a wall of the colon 156 (e.g., the superior wall of the rectum 160), the biological navigation device 10 can then track to the wall of the colon 156.

FIG. 27d illustrates that after making a turn in the rectum 160, the distal end of the biological navigation device 10 can be further extended, as shown by arrow, or translated into and through the sigmoid colon 162, for example as additional cells 14 are inflated and longitudinally expanded. The cells 14 can be expanded in or out of longitudinal order (i.e., most distal to most proximal). For example, the two most distal cells 14 can be alternately inflated and deflated to inchworm or help loosen or ease navigation of the distal end of the biological navigation device 10.

Figure 27E:
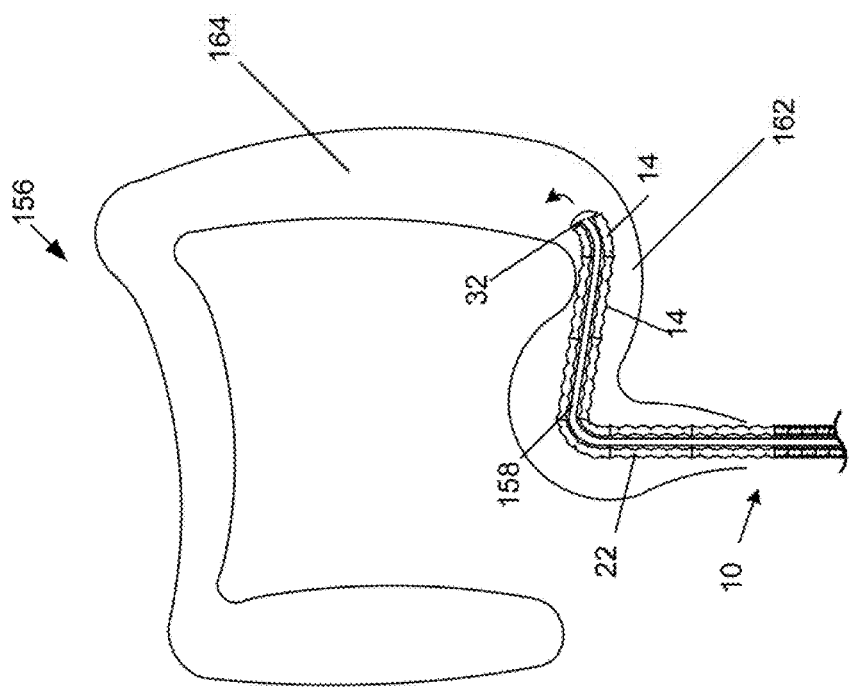

FIG. 27e illustrates that the biological navigation device 10 can make a turn, as shown by arrow, for example as the biological navigation device 10 passes from the sigmoid colon 162 to the descending colon 164. FIG. 43f illustrates that the biological navigation device 10 can be further advanced, extended or translated, as shown by arrow, for example by inflating additional cells 14, through the descending colon 164 after the biological navigation device 10 has made two previous turns.

The biological navigation device 10 can be repeatedly turned and advanced, for example by inflating the cells 14 and/or controlling the articulatable section 66 and/or the elongated element 28 otherwise, to extend as far along the colon 156 as desired.

At any length in the colon 156, the biological navigation device 10 or elongated element 28, for example at the distal component 32 of the elongated element 28, can gather diagnostic (e.g., sensing) data, such as data for visualization, tissue inductance, RF absorption or combinations thereof. The biological navigation device 10 and/or elongated element 28 can also gather tissue samples (e.g., by performing a biopsy or removing a polyp). At any length in the colon 156, the biological navigation device 10 and/or elongated element 28, for example at the distal component 32, can perform treatment or therapy, such as delivery of a drug onto or into tissue, tissue removal (e.g., polyp or tumor removal), or combinations thereof.

FIG. 27g illustrates that the biological navigation device 10 can be advanced along the entire colon 156, passing through the rectum 160, sigmoid colon 162, descending colon 164, transverse colon 166, ascending colon 168, and having the tip distal end in the cecum 170. The biological navigation device 10 can be withdrawn, as shown by arrows, from the colon 156, for example by applying a tensile force against the tube 12 and/or elongated element 28, as shown by arrows 172 and/or deflating the cells 14. The biological navigation device 10 can be withdrawn, as shown by arrows, from the colon 156, for example by applying a tensile force to the umbilical(s) 158.

FIG. 27h illustrates that the cells 14 at the proximal end of the biological navigation device 10 can be inflated or otherwise extended before the cells 14 at the distal end of the biological navigation device 10. For example, the cells 14 can be sequentially inflated or extended from the proximal-most cell 14 to the distal-most cell 14 (also as shown in FIG. 10a). Alternatively, the cells 14 can be sequentially inflated or extended from the distal-most cell 14 to the proximal-most cell 14 or in an order not in a sequential order of the cell 14 location along the length of the biological navigation device 10.

The biological navigation device 10 can be manually and/or actuator controlled. Control inputs can be delivered through a manually actuated controllable module, such as a joystick (e.g., for tip control) and/or a series of linear and rotary potentiometers and switches. The biological navigation device 10 can be programmed to be controlled by voice commands. The biological navigation device 10 can be controlled by a foot pedal (e.g., for tube extension or translation), and/or a combinational interface (e.g., hand controlled), for example for tip control. The user interface can be attached as part of the biological navigation device 10, and/or the user interface can be a control unit that is attached by wires to the biological navigation device 10, and/or the user interface can communicate wirelessly with the remainder of the biological navigation device 10.

Any or all elements of the biological navigation device 10 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft) any of the other materials listed herein or combinations thereof. Examples of radiopaque materials are barium sulfate, zinc oxide, titanium, stainless steel, nickel-titanium alloys, tantalum and gold.

The systems, devices, elements and methods disclosed herein can be used in conjunction or substituted with any of the systems, devices, elements and methods disclosed in Provisional Patent Application Nos. 60/887,323, filed 30 Jan. 2007; and 60/949,219, filed 11 Jul. 2007; U.S. patent application titled "Biological Navigation Device", attorney docket number LMVSNZ00200, filed concurrently herewith; and PCT Application titled "Biological Navigation Device", attorney docket number LMVSNZ00500WO, filed concurrently herewith, which are all incorporated herein by reference in their entireties. The everting element can be merely representative of any pressurized tube 12, including those disclosed in the references incorporated, supra.

The term colonoscope is used for exemplary purposes and can be any deployable elongated element 28 for use in a body lumen, such as an endoscope. The pressurizer can be the deployment system. The terms tip, tool tip, tip distal end, and tool head are used interchangeably herein.

The tube 12 can have wide medical applicability, including, but not limited to, endoscopy and the dilation of anatomical structures. One such dilation application is for use in the field of interventional cardiology, where they can be used for lesion dilation, as a stand-alone procedure, for pre-stent deployment ('pre-dil'), for post-stent deployment, as part of a stent-expansion inflatable structure used as a stent delivery system, or combinations thereof.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A device for navigation through a biological anatomy, the device comprising:
    a tube configured to be advanced through the biological anatomy, the tube having a tube lumen therein;
    a steering portion configured to bend to orient the device, said steering portion comprising an actuator for controlling the steering portion;
    a reciprocating portion comprising a first tubular reciprocating element and a second tubular reciprocating element, the first tubular reciprocating element attached to a distal end of the steering portion, the second tubular reciprocating element mounted to and surrounding the first tubular reciprocating element, wherein an entirety of the second tubular reciprocating element is configured to longitudinally translate relative to the first tubular reciprocating element, wherein the second tubular reciprocating element remains coaxial with the first tubular reciprocating element during longitudinal translation of the second tubular reciprocating element relative to the first reciprocating element;
    a visualization element for visualizing the biological anatomy; and
    a distal tip at a distal end of the second tubular reciprocating element having a tip lumen therein continuous with the tube lumen, the tip lumen configured to hold the visualization element therein;
    wherein longitudinal translation of the second tubular reciprocating element causes corresponding longitudinal translation of the visualization element held within the tip lumen of the distal tip.

2. The device of claim 1, wherein the steering portion includes an articulating portion.

3. The device of claim 2, wherein the articulating portion includes at least three articulable links that are concurrently articulatable and controlled by a control cable serving as the actuator.

4. The device of claim 1, wherein the tube is configured to be pressurizably advanced through the biological anatomy.

5. The device of claim 1, further comprising a reciprocating actuator connected to the reciprocating portion configured to actuate the reciprocating portion.

6. The device of claim 2, wherein the articulating portion comprises a first link received within a portion of a second link such that the first link may articulate relative to the second link.

7. The device of claim 1, wherein the steering portion, the reciprocating portion and the distal tip are connected in series.

8. The device of claim 1, wherein the visualization element comprises a camera.

9. A device for navigation through a biological anatomy, the device comprising:
    a tube configured to be advanced through the biological anatomy, the tube having a tube lumen therein;
    a steering portion configured to bend to orient the device;
    an actuator for actuating the steering portion to control the orientation of the device;
    a reciprocating portion comprising a first tubular reciprocating element and a second tubular reciprocating element, the first tubular reciprocating element attached to a distal end of the steering portion, the second tubular reciprocating element mounted to the first tubular reciprocating element, wherein an entirety of the second tubular reciprocating element is configured to longitudinally translate relative to the first tubular reciprocating element, wherein the second tubular reciprocating element remains coaxial with the first tubular reciprocating element during longitudinal translation of the second tubular reciprocating element relative to the first reciprocating element; and
    a distal tip at a distal end of the second tubular reciprocating element having a tip lumen therein continuous with the tube lumen, the tip lumen configured to hold a visualization element therein;

wherein longitudinal translation of the second tubular reciprocating element causes corresponding longitudinal translation of the visualization element held within the tip lumen of the distal tip.

10. The device of claim 9, wherein the steering portion, the reciprocating portion and the distal tip are connected in series.

11. A device for navigation through a biological anatomy, the device comprising:
   a tube configured to be advanced through the biological anatomy, the tube having a tube lumen therein;
   a steering portion configured to bend to orient the device, the steering portion comprising a plurality of pivotable links connected by a control cable;
   a reciprocating portion comprising a first tubular reciprocating element and a second tubular reciprocating element, the first tubular reciprocating element attached to a distal end of the steering portion, the second tubular reciprocating element mounted to and surrounding the first tubular reciprocating element, wherein the second tubular reciprocating element is configured to longitudinally translate relative to the first tubular reciprocating element, wherein the second tubular reciprocating element remains coaxial with the first tubular reciprocating element during longitudinal translation of the second tubular reciprocating element relative to the first reciprocating element; and
   a distal tip at a distal end of the second tubular reciprocating element having a tip lumen therein continuous with the tube lumen, the tip lumen configured to hold a visualization element therein;
   wherein longitudinal translation of the second tubular reciprocating element causes corresponding longitudinal translation of the visualization element held within the tip lumen of the distal tip.

12. The device of claim 11, wherein the steering portion, the reciprocating portion and the distal tip are connected in series.

* * * * *